United States Patent [19]
Ramsey

[11] Patent Number: 5,858,195
[45] Date of Patent: Jan. 12, 1999

[54] APPARATUS AND METHOD FOR PERFORMING MICROFLUIDIC MANIPULATIONS FOR CHEMICAL ANALYSIS AND SYNTHESIS

[75] Inventor: J. Michael Ramsey, Knoxville, Tenn.

[73] Assignee: Lockheed Martin Energy Research Corporation, Oak Ridge, Tenn.

[21] Appl. No.: 776,645

[22] PCT Filed: Aug. 1, 1995

[86] PCT No.: PCT/US95/09492

§ 371 Date: Feb. 3, 1997

§ 102(e) Date: Feb. 3, 1997

[87] PCT Pub. No.: WO96/04547

PCT Pub. Date: Feb. 15, 1996

Related U.S. Application Data

[63] Continuation-in-part of Ser. No. 283,769, Aug. 1, 1994.

[51] Int. Cl.$^6$ .......................... G01N 27/26; G01N 27/447
[52] U.S. Cl. ......................... 204/601; 204/450; 204/451; 204/600
[58] Field of Search ..................... 204/450, 451, 204/452, 453, 455, 600, 601, 602, 603, 604, 605

[56] References Cited

U.S. PATENT DOCUMENTS

| | | | |
|---|---|---|---|
| 4,390,403 | 6/1983 | Batchelder | 204/547 |
| 4,908,112 | 3/1990 | Pace | 204/601 X |
| 5,073,239 | 12/1991 | Hjerten | 204/453 |
| 5,092,973 | 3/1992 | Zare et al. | 204/452 |
| 5,110,431 | 5/1992 | Moring | 204/451 |
| 5,126,022 | 6/1992 | Soane et al. | 204/458 |
| 5,132,012 | 7/1992 | Miura et al. | 210/198 Z |
| 5,141,621 | 8/1992 | Zare et al. | 204/453 |
| 5,180,480 | 1/1993 | Manz | 204/299 R |
| 5,229,297 | 7/1993 | Schnipelsky et al. | 436/94 |
| 5,250,263 | 10/1993 | Manz | 422/81 |
| 5,288,463 | 2/1994 | Chemelli | 422/58 |
| 5,296,114 | 3/1994 | Manz | 204/180.1 |
| 5,376,252 | 12/1994 | Ekstrom et al. | 204/604 X |
| 5,429,734 | 7/1995 | Gajar et al. | 204/603 |
| 5,585,069 | 12/1996 | Zanzucchi et al. | 422/100 |
| 5,603,351 | 2/1997 | Cherukuri et al. | 137/597 |
| 5,605,662 | 2/1997 | Heller et al. | 422/68.1 |
| 5,750,015 | 5/1998 | Soane et al. | 204/454 |

FOREIGN PATENT DOCUMENTS

| | | |
|---|---|---|
| 0 356 160 A2 | 2/1990 | European Pat. Off. . |
| 0 620 432 A1 | 4/1993 | European Pat. Off. . |
| 620432 | 10/1994 | European Pat. Off. . |
| 2 191 110 | 12/1987 | United Kingdom . |

OTHER PUBLICATIONS

M. Deml, F. Foret and P. Bozek "Electric Sample Splitter for Capillary Electrophoresis" Journal of Chromatography, 320 (1985) 159–165.

Manz, et al., "Micromachining of Monocrystalline Silicon and Glass for Chemical Analysis Systems", *Trends in Analytical Chemistry*, vol. 10 No. 5, pp. 144–149 (1991).

(List continued on next page.)

*Primary Examiner*—Robert J. Warden
*Assistant Examiner*—John S. Starsiak, Jr.
*Attorney, Agent, or Firm*—Dann, Dorfman, Herrell and Skillman

[57] ABSTRACT

A microchip laboratory system and method provide fluid manipulations for a variety of applications, including sample injection for microchip chemical separations. The microchip is fabricated using standard photolithographic procedures and chemical wet etching, with the substrate and cover plate joined using direct bonding. Capillary electrophoresis and electrochromatography are performed in channels formed in the substrate. Analytes are loaded into a four-way intersection of channels by electrokinetically pumping the analyte through the intersection, followed by switching of the potentials to force an analyte plug into the separation channel.

25 Claims, 21 Drawing Sheets

OTHER PUBLICATIONS

Seiler, et al., "Planar Glass chips for Capillary Electrophoresis: Repetitive Sample Injection, Quantitation, and Separation Efficiency", *Analytical Chemistry*, vol. 65, No. 10 pp. 1481–1488 (1993).

Zhonghul, et al. "Micromachining of Capillary Electrophoresis Injectors and Separators on Glass Chips and Evaluation of Flow at Capillary Intersections", *Analytical Chemistry*, vol. 66, No. 1, pp. 177–184 (1994).

Jacobson, et al., "High–Speed Separations on a Microchip". *Analytical Chemistry*, vol. 66, No. 7., pp. 1114–1118 (1994).

Dasgupta, et al., "Electroosmosis: A Reliable Fluid Propulsion System for Flow Injection Analysis". *Analytical Chemistry*, pp. 1792–1798 (1995).

D. Jed Harrison, Karl Fluri, Kurt Seiler, Zhonghui Fan, Carlo S. Effenhauser, Andreas Manz, "Micromachining a Miniaturized Capillary Electrophoresis Based Chemical Analysis System in a Chip" Science, vol. 261 (Aug. 13, 1993) 895–897.

Stephen C. Jacobson et al, "Effects of Injection Schemes and Column Geometry on the Performance of Microchip Electrophoresis Devices" Analytical Chemistry, vol. 66, No. 7 (Apr. 1994)1107–1113.

D. Jed Harrison et al, "Capillary Electrophoresis and Sample Injection Systems Integrated on a Planar Glass Chip" Analytical Chemistry, vol. 64, No. 17 (Sep. 1992)1926–1932.

Carlo S. Effenhauser et al, "Glass Chips for High–Speed Capillary Electrophoresis Separations with Submicrometer Plate Heights" Analytical Chemistry, vol. 65, No. 19 (Oct. 1993)2637–2642.

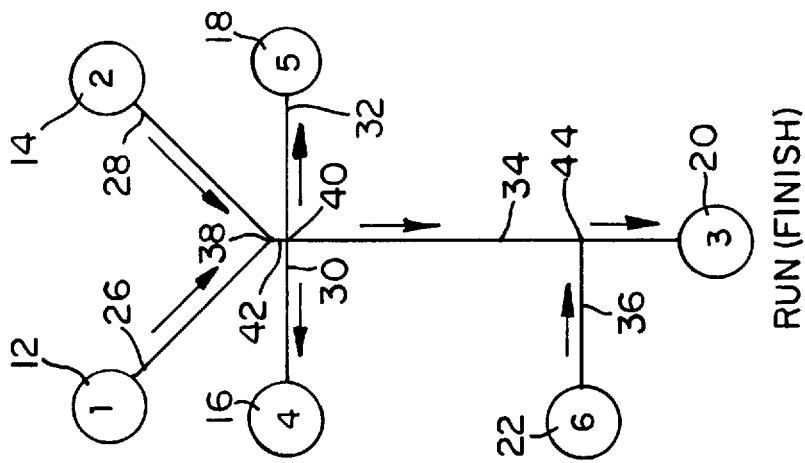
FIG. 31C RUN (FINISH)
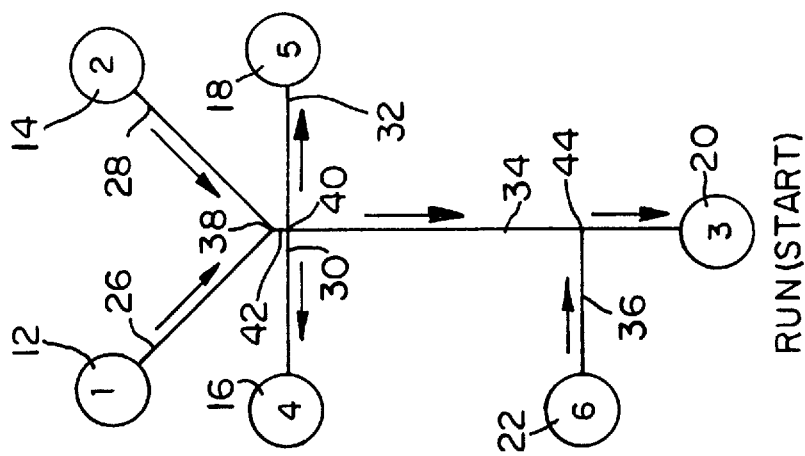
FIG. 31B RUN (START)
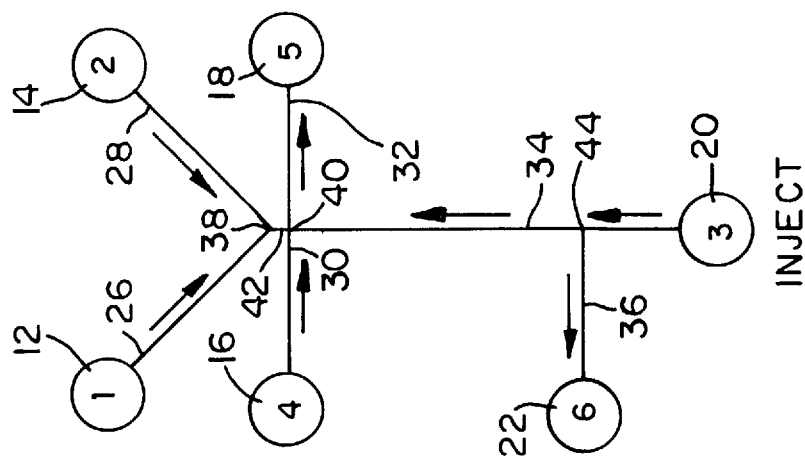
FIG. 31A INJECT

APPARATUS AND METHOD FOR PERFORMING MICROFLUIDIC MANIPULATIONS FOR CHEMICAL ANALYSIS AND SYNTHESIS This application is a 371 of PCT/US95/09492 filed Aug. 1, 1995 and a continuation-in-part of U.S. application Ser. No. 08/283,769, filed Aug. 1, 1994.

This invention was made with Government support under contract DE-AC05-89OR21400 awarded by the U.S. Department of Energy to Martin Marietta Energy Systems, Inc. and the Government has certain rights in this invention.

FIELD OF THE INVENTION

The present invention relates generally to miniature instrumentation for chemical analysis, chemical sensing and synthesis and, more specifically, to electrically controlled manipulations of fluids in micromachined channels. These manipulations can be used in a variety of applications, including the electrically controlled manipulation of fluid for capillary electrophoresis, liquid chromatography, flow injection analysis, and chemical reaction and synthesis.

BACKGROUND OF THE INVENTION

Laboratory analysis is a cumbersome process. Acquisition of chemical and biochemical information requires expensive equipment, specialized labs and highly trained personnel. For this reason, laboratory testing is done in only a fraction of circumstances where acquisition of chemical information would be useful. A large proportion of testing in both research and clinical situations is done with crude manual methods that are characterized by high labor costs, high reagent consumption, long turnaround times, relative imprecision and poor reproducibility. The practice of techniques such as electrophoresis that are in widespread use in biology and medical laboratories have not changed significantly in thirty years.

Operations that are performed in typical laboratory processes include specimen preparation, chemical/biochemical conversions, sample fractionation, signal detection and data processing. To accomplish these tasks, liquids are often measured and dispensed with volumetric accuracy, mixed together, and subjected to one or several different physical or chemical environments that accomplish conversion or fractionation. In research, diagnostic, or development situations, these operations are carried out on a macroscopic scale using fluid volumes in the range of a few microliters to several liters at a time. Individual operations are performed in series, often using different specialized equipment and instruments for separate steps in the process. Complications, difficulty and expense are often the result of operations involving multiple laboratory processing steps.

Many workers have attempted to solve these problems by creating integrated laboratory systems. Conventional robotic devices have been adapted to perform pipetting, specimen handling, solution mixing, as well as some fractionation and detection operations. However, these devices are highly complicated, very expensive and their operation requires so much training that their use has been restricted to a relatively small number of research and development programs. More successful have been automated clinical diagnostic systems for rapidly and inexpensively performing a small number of applications such as clinical chemistry tests for blood levels of glucose, electrolytes and gases. Unfortunately due to their complexity, large size and great cost, such equipment, is limited in its application to a small number of diagnostic circumstances.

The desirability of exploiting the advantages of integrated systems in a broader context of laboratory applications has led to proposals that such systems be miniaturized. In the 1980's, considerable research and development effort was put into an exploration of the concept of biosensors with the hope they might fill the need. Such devices make use of selective chemical systems or biomolecules that are coupled to new methods of detection such as electrochemistry and optics to transduce chemical signals to electrical ones that can be interpreted by computers and other signal processing units. Unfortunately, biosensors have been a commercial disappointment. Fewer than 20 commercialized products were available in 1993, accounting for revenues in the U.S. of less than $ 100 million. Most observers agree that this failure is primarily technological rather than reflecting a misinterpretation of market potential. In fact, many situations such as massive screening for new drugs, highly parallel genetic research and testing, micro-chemistry to minimize costly reagent consumption and waste generation, and bedside or doctor's office diagnostics would greatly benefit from miniature integrated laboratory systems.

In the early 1990's, people began to discuss the possibility of creating miniature versions of conventional technology. Andreas Manz was one of the first to articulate the idea in the scientific press. Calling them "miniaturized total analysis systems," or "$\mu$-TAS," he predicted that it would be possible to integrate into single units microscopic versions of the various elements necessary to process chemical or biochemical samples, thereby achieving automated experimentation. Since that time, miniature components have appeared, particularly molecular separation methods and microvalves. However, attempts to combine these systems into completely integrated systems have not net with success. This is primarily because precise manipulation of tiny fluid volumes in extremely narrow channels has proven to be a difficult technological hurdle.

One prominent field susceptible to miniaturization is capillary electrophoresis. Capillary electrophoresis has become a popular technique for separating charged molecular species in solution. The technique is performed in small capillary tubes to reduce band broadening effects due to thermal convection and hence improve resolving power. The small tubes imply that minute volumes of materials, on the order of nanoliters, must be handled to inject the sample into the separation capillary tube.

Current techniques for injection include electromigration and siphoning of sample from a container into a continuous separation tube. Both of these techniques suffer from relatively poor reproducibility, and electromigration additionally suffers from electrophoretic mobility-based bias. For both sampling techniques the input end of the analysis capillary tube must be transferred from a buffer reservoir to a reservoir holding the sample. Thus, a mechanical manipulation is involved. For the siphoning injection, the sample reservoir is raised above the buffer reservoir holding the exit end of the capillary for a fixed length of time.

An electromigration injection is effected by applying an appropriately polarized electrical potential across the capillary tube for a given duration while the entrance end of the capillary is in the sample reservoir. This can lead to sampling bias because a disproportionately larger quantity of the species with higher electrophoretic mobilities migrate into the tube. The capillary is removed from the sample reservoir and replaced into the entrance buffer reservoir after the injection duration for both techniques.

A continuing need exists for methods and apparatuses which lead to improved electrophoretic resolution and improved injection stability.

SUMMARY OF THE INVENTION

The present invention provides microchip laboratory systems and methods that allow complex biochemical and chemical procedures to be conducted on a microchip under electronic control. The microchip laboratory systems comprises a material handling apparatus that transports materials through a systems of interconnected, integrated channels on a microchip. The movement of the materials is precisely directed by controlling the electric fields produced in the integrated channels. The precise control of the movement of such materials enables precise mixing, separation, and reaction as needed to implement a desired biochemical or chemical procedure.

The microchip laboratory system of the present invention analyzes and/or synthesizes chemical materials in a precise and reproducible manner. The system includes a body having integrated channels connecting a plurality of reservoirs that store the chemical materials used in the chemical analysis or synthesis performed by the system. In one aspect, at least five of the reservoirs simultaneously have a controlled electrical potential, such that material from at least one of the reservoirs is transported through the channels toward at least one of the other reservoirs. The transportation of the material through the channels provides exposure to one or more selected chemical or physical environments, thereby resulting in the synthesis or analysis of the chemical material.

The microchip laboratory system preferably also includes one or more intersections of integrated channels connecting three or more of the reservoirs. The laboratory system controls the electric fields produced in the channels in a manner that controls which materials in the reservoirs are transported through the intersection(s). In one embodiment, the microchip laboratory system acts as a mixer or diluter that combines materials in the intersection(s) by producing an electrical potential in the intersection that is less than the electrical potential at each of the two reservoirs from which the materials to be mixed originate. Alternatively, the laboratory system can act as a dispenser that electrokinetically injects precise, controlled amounts of material through the intersection(s).

By simultaneously applying an electrical potential at each of at least five reservoirs, the microchip laboratory system can act as a complete system for performing an entire chemical analysis or synthesis. The five or more reservoirs can be configured in a manner that enables the electrokinetic separation of a sample to be analyzed ("the analyte") which is then mixed with a reagent from a reagent reservoir. Alternatively, a chemical reaction of an analyte and a solvent can be performed first, and then the material resulting from the reaction can be electrokinetically separated. As such, the use of five or more reservoirs provides an integrated laboratory system that can perform virtually any chemical analysis or synthesis.

In yet another aspect of the invention, the microchip laboratory system includes a double intersection formed by channels interconnecting at least six reservoirs. The first intersection can be used to inject a precisely sized analyte plug into a separation channel toward a waste reservoir. The electrical potential at the second intersection can be selected in a manner that provides additional control over the size of the analyte plug. In addition, the electrical potentials can be controlled in a manner that transports materials from the fifth and sixth reservoirs through the second intersection toward the first intersection and toward the fourth reservoir after a selected volume of material from the first intersection is transported through the second intersection toward the fourth reservoir. Such control can be used to push the analyte plug further down the separation channel while enabling a second analyte plug to be injected through the first intersection.

In another aspect, the microchip laboratory system acts as a microchip flow control system to control the flow of material through an intersection formed by integrated channels connecting at least four reservoirs. The microchip flow control system simultaneously applies a controlled electrical potential to at least three of the reservoirs such that the volume of material transported from the first reservoir to a second reservoir through the intersection is selectively controlled solely by the movement of a material from a third reservoir through the intersection. Preferably, the material moved through the third reservoir to selectively control the material transported from the first reservoir is directed toward the same second reservoir as the material from the first reservoir. As such, the microchip flow control system acts as a valve or a gate that selectively controls the volume of material transported through the intersection The microchip flow control system can also be configured to act as a dispenser that prevents the first material from moving through the intersection toward the second reservoir after a selected volume of the first material has passed through the intersection. Alternatively, the microchip flow control system can be configured to act as a diluter that mixes the first and second materials in the intersection in a manner that simultaneously transports the first and second materials from the intersection toward the second reservoir.

Other objects, advantages and salient features of the invention will become apparent from the following detailed description, which taken in conjunction with the annexed drawings, discloses preferred embodiments of the invention

BRIEF DESCRIPTION OF THE DRAWINGS

FIG. 31 is a schematic view of the apparatus of FIG. 21, showing sequential applications of voltages to effect desired fluidic manipulations.

DETAILED DESCRIPTION OF THE INVENTION

Integrated, micro-laboratory systems for analyzing or synthesizing chemicals require a precise way of manipulating fluids and fluid-borne material and subjecting the fluids to selected chemical or physical environments that produce desired conversions or partitioning. Given the concentration of analytes that produces chemical conversion in reasonable time scales, the nature of molecular detection, diffusion times and manufacturing methods for creating devices on a microscopic scale, miniature integrated micro-laboratory systems lend themselves to channels having dimensions on the order of 1 to 100 micrometers in diameter. Within this context, electrokinetic pumping has proven to be versatile and effective in transporting materials in microfabricated laboratory systems.

The present invention provides the tools necessary to make use of electrokinetic pumping not only in separations, but also to perform liquid handling that accomplishes other important sample processing steps, such as chemical conversions or sample partitioning. By simultaneously controlling voltage at a plurality of ports connected by channels in a microchip structure, it is possible to measure and dispense fluids with great precision, mix reagents, incubate reaction components, direct the components towards sites of physical or biochemical partition and subject the components to detector systems. By combining these capabilities on a single microchip, one is able to create complete, miniature, integrated automated laboratory systems for analyzing or synthesizing chemicals.

Such integrated micro-laboratory systems can be made up of several component elements. Component elements can include liquid dispensing systems, liquid mixing systems, molecular partition systems, detector sights, etc. For example, as described herein, one can construct a relatively complete system for the identification of restriction endonuclease sites in a DNA molecule. This single microfabricated device thus includes in a single system the functions that are traditionally performed by a technician employing pipettors, incubators, gel electrophoresis systems, and data acquisition systems. In this system, DNA is mixed with an enzyme, the mixture is incubated, and a selected volume of the reaction mixture is dispensed into a separation channel. Electrophoresis is conducted concurrent with fluorescent labeling of the DNA.

Figure 1:
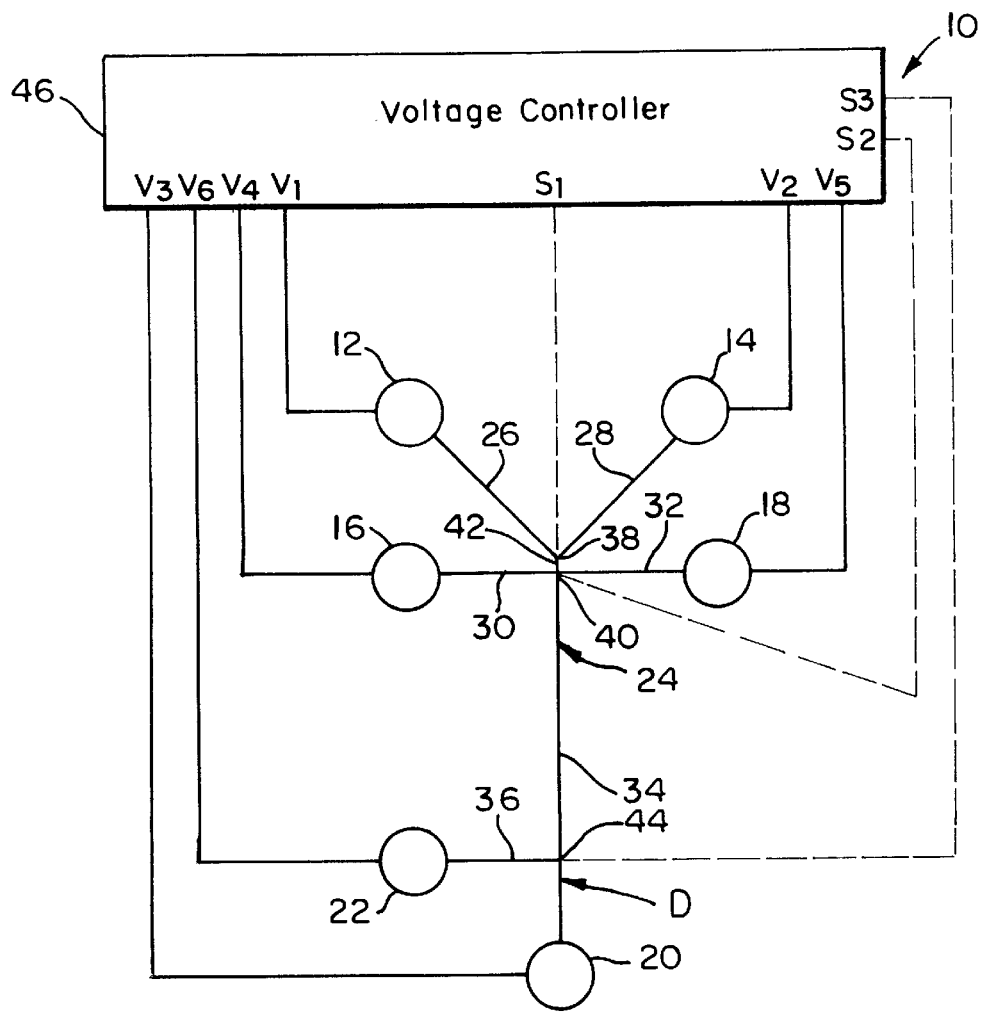
FIG. 1 is a schematic view of a preferred embodiment of the present invention.

Shown in FIG. 1 is an example of a microchip laboratory system 10 configured to implement an entire chemical analysis or synthesis. The laboratory system includes six reservoirs 12, 14, 16, 18, 20, and 22 connected to each other by a system of channels 24 micromachined into a substrate or base member (not shown in FIG. 1), as discussed in more detail below. Each reservoir 12–22 is in fluid communication with a corresponding channel 26, 28, 30, 32, 34, 36, and 38 of the channel system 24. The first channel 26 leading from the first reservoir 12 is connected to the second channel 28 leading from the second reservoir 14 at a first intersection 38. Likewise, the third channel 30 from the third reservoir 16 is connected to the fourth channel 32 at a second intersection 40. The first intersection 38 is connected to the second intersection 40 by a reaction chamber or channel 42. The fifth channel 34 from the fifth reservoir 20 is also connected to the second intersection 40 such that the second intersection 40 is a four-way intersection of channels 30, 32, 34, and 42. The fifth channel 34 also intersects the sixth channel 36 from the sixth reservoir 22 at a third intersection 44.

The materials stored in the reservoirs preferably are transported electrokinetically through the channel system 24 in order to implement the desired analysis or synthesis. To provide such electrokinetic transport, the laboratory system 10 includes a voltage controller 46 capable of applying selectable voltage levels, including ground. Such a voltage controller can be implemented using multiple voltage dividers and multiple relays to obtain the selectable voltage levels. The voltage controller is connected to an electrode positioned in each of the six reservoirs 12–22 by voltage lines V1–V6 in order to apply the desired voltages to the materials in the reservoirs. Preferably, the voltage controller also includes sensor channels S1, S2, and S3 connected to the first, second, and third intersections 38, 40, 44, respectively, in order to sense the voltages present at those intersections.

The use of electrokinetic transport on microminiaturized planar liquid phase separation devices, described above, is a viable approach for sample manipulation and as a pumping mechanism for liquid chromatography. The present invention also entails the use of electroosmotic flow to mix various fluids in a controlled and reproducible fashion. When an appropriate fluid is placed in a tube made of a correspondingly appropriate material, functional groups at the surface of the tube can ionize. In the case of tubing materials that are terminated in hydroxyl groups, protons will leave the surface and enter an aqueous solvent. Under such conditions the surface will have a net negative charge and the solvent will have an excess of positive charges, mostly in the charged double layer at the surface. With the application of an electric field across the tube, the excess cations in solution will be attracted to the cathode, or negative electrode. The movement of these positive charges through the tube will drag the solvent with them. The steady state velocity is given by equation 1, $$v = \frac{\epsilon \xi E}{4\pi \eta} \quad (1)$$

where v is the solvent velocity, $\epsilon$ is the dielectric constant of the fluid, $\xi$ is the zeta potential of the surface, E is the electric field strength, and $\eta$ is the solvent viscosity. From equation 1 it is obvious that the fluid flow velocity or flow rate can be controlled through the electric field strength. Thus, electroosmosis can be used as a programmable pumping mechanism.

The laboratory microchip system 10 shown in FIG. 1 could be used for performing numerous types of laboratory analysis or synthesis, such as DNA sequencing or analysis, electrochromatography, micellar electrokinetic capillary chromatography (MECC), inorganic ion analysis, and gradient elution liquid chromatography, as discussed in more detail below. The fifth channel 34 typically is used for electrophoretic or electrochromatographic separations and thus may be referred to in certain embodiments as a separation channel or column. The reaction chamber 42 can be used to mix any two chemicals stored in the first and second reservoirs 12, 14. For example, DNA from the first reservoir 12 could be mixed with an enzyme from the second reservoir 14 in the first intersection 38 and the mixture could be incubated in the reaction chamber 42. The incubated mixture could then be transported through the second intersection 40 into the separation column 34 for separation. The sixth reservoir 22 can be used to store a fluorescent label that is mixed in the third intersection 44 with the materials separated in the separation column 34. An appropriate detector (D) could then be employed to analyze the labeled materials between the third intersection 44 and the fifth reservoir 20. By providing for a pre-separation column reaction in the first intersection 38 and reaction chamber 42 and a post-separation column reaction in the third intersection 44, the laboratory system 10 can be used to implement many standard laboratory techniques normally implemented manually in a conventional laboratory. In addition, the elements of the laboratory system 10 could be used to build a more complex system to solve more complex laboratory procedures.

The laboratory microchip system 10 includes a substrate or base member (not shown in FIG. 1) which can be an approximately two inch by one inch piece of microscope slide (Corning, Inc. #2947). While glass is a preferred material, other similar materials may be used, such as fused silica, crystalline quartz, fused quartz, plastics, and silicon (if the surface is treated sufficiently to alter its resistivity). Preferably, a non-conductive material such as glass or fused quartz is used to allow relatively high electric fields to be applied to electrokinetically transport materials through channels in the microchip. Semiconducting materials such as silicon could also be used, but the electric field applied would normally need to be kept to a minimum (approximately less than 300 volts per centimeter using present techniques of providing insulating layers), which may provide insufficient electrokinetic movement.

The channel pattern 24 is formed in a planar surface of the substrate using standard photolithographic procedures followed by chemical wet etching. The channel pattern may be transferred onto the substrate with a positive photoresist (Shipley 1811) and an e-beam written chrome mask (Institute of Advanced Manufacturing Sciences, Inc.). The pattern may be chemically etched using $HF/NH_4F$ solution.

After forming the channel pattern, a cover plate may then be bonded to the substrate using a direct bonding technique whereby the substrate and the cover plate surfaces are first hydrolyzed in a dilute $NH_4OH/H_2O_2$ solution and then joined. The assembly is then annealed at about 500° C. in order to insure proper adhesion of the cover plate to the substrate.

Following bonding of the cover plate, the reservoirs are affixed to the substrate, with portions of the cover plate sandwiched therebetween, using epoxy or other suitable means. The reservoirs can be cylindrical with open opposite axial ends. Typically, electrical contact is made by placing a platinum wire electrode in each reservoirs. The electrodes are connected to a voltage controller 46 which applies a desired potential to select electrodes, in a manner described in more detail below.

Figure 2:
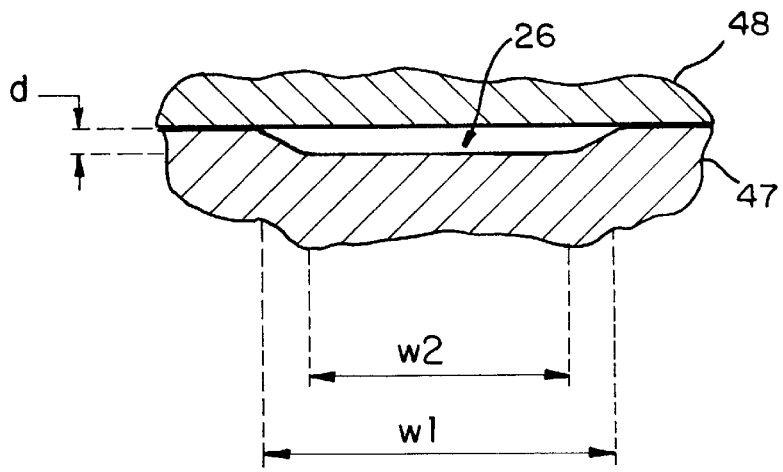
FIG. 2 is an enlarged, vertical sectional view of a channel shown.

A cross section of the first channel is shown in FIG. 2 and is identical to the cross section of each of the other integrated channels. When using a non-crystalline material (such as glass) for the substrate, and when the channels are chemically wet etched, an isotropic etch occurs, i.e., the glass etches uniformly in all directions, and the resulting channel geometry is trapezoidal. The trapezoidal cross section is due to "undercutting" by the chemical etching process at the edge of the photoresist. In one embodiment, the channel cross section of the illustrated embodiment has dimensions of 5.2 µm in depth, 57 82 m in width at the top and 45 82 m in width at the bottom. In another embodiment, the channel has a depth "d" of 10 82 m, an upper width "w1" of 90 µm, and a lower width "w2" of 70 µm.

An important aspect of the present invention is the controlled electrokinetic transportation of materials through the channel system 24. Such controlled electrokinetic transport can be used to dispense a selected amount of material from one of the reservoirs through one or more intersections of the channel structure 24. Alternatively, as noted above, selected amounts of materials from two reservoirs can be transported to an intersection where the materials can be mixed in desired concentrations.

Gated Dispenser

Figure 3:
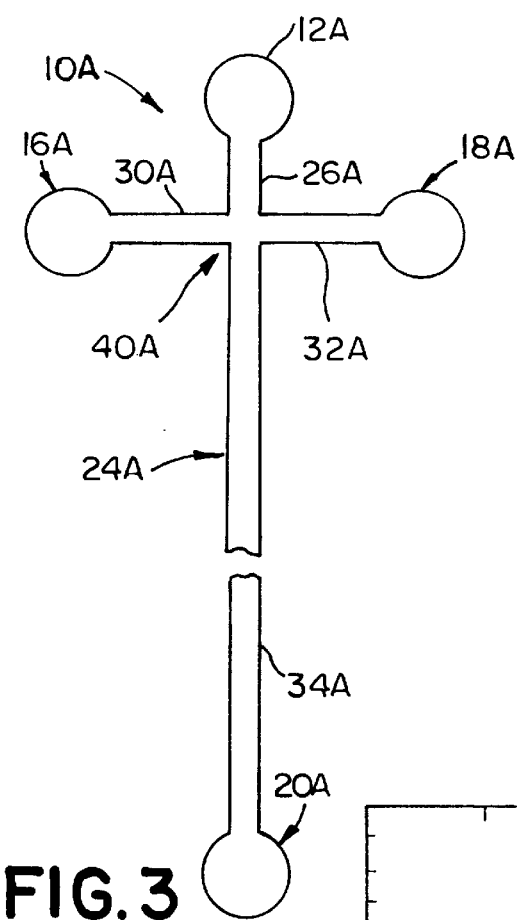
FIG. 3 is a schematic, top view of a microchip according to a second preferred embodiment of the present invention.

Shown in FIG. 3 is a laboratory component 10A that can be used to implement a preferred method of transporting materials through a channel structure 24A. The A following each number in FIG. 3 indicates that it corresponds to an analogous element of FIG. 1 of the same number without the A. For simplicity, the electrodes and the connections to the voltage controller that controls the transport of materials through the channel System 24A are not shown in FIG. 3.

The microchip laboratory system 10A shown in FIG. 3 controls the amount of material from the first reservoir 12A transported through the intersection 40A toward the fourth reservoir 20A by electrokinetically opening and closing access to the intersection 40A from the first channel 26A. As such, the laboratory microchip system 10A essentially implements a controlled electrokinetic valve. Such an electrokinetic valve can be used as a dispenser to dispense selected volumes of a single material or as a mixer to mix selected volumes of plural materials in the intersection 40A. In general, electro-osmosis is used to transport "fluid materials" and electrophoresis is used to transport ions without transporting the fluid material surrounding the ions. Accordingly, as used herein, the term "material" is used broadly to cover any form of material, including fluids and ions.

The laboratory system 10A provides a continuous unidirectional flow of fluid through the separation channel 34A. This injection or dispensing scheme only requires that the voltage be changed or removed from one (or two) reservoirs and allows the fourth reservoir 20A to remain at ground potential. This will allow injection and separation to be performed with a single polarity power supply.

Figure 4:
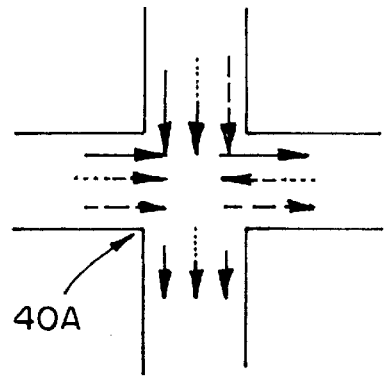
FIG. 4 is an enlarged view of the intersection region of FIG. 3.

An enlarged view of the intersection 40A is shown in FIG. 4. The directional arrows indicate the time sequence of the flow profiles at the intersection 40A. The solid arrows show the initial flow pattern. Voltages at the various reservoirs are adjusted to obtain the described flow patterns. The initial flow pattern brings a second material from the second reservoir 16A at a sufficient rate such that all of the first material transported from reservoir 12A to the intersection 40A is pushed toward the third reservoir 18A. In general, the potential distribution will be such that the highest potential is in the second reservoir 16A, a slightly lower potential in the first reservoir 12A, and yet a lower potential in the third reservoir 18A, with the fourth reservoir 20A being grounded. Under these conditions, the flow towards the fourth reservoir 20A is solely the second material from the second reservoir 16A.

To dispense material from the first reservoir 12A through the intersection 40A, the potential at the second reservoir 16A can be switched to a value less than the potential of the first reservoir 12A or the potentials at reservoirs 16A and/or 18A, can be floated momentarily to provide the flow shown by the short dashed arrows in FIG. 4. Under these conditions, the primary flow will be from the first reservoir 12A down towards the separation channel waste reservoir 20A. The flow from the second and third reservoirs 16A, 18A will be small and could be in either direction. This condition is held long enough to transport a desired amount of material from the first reservoir 12A through the intersection 40A and into the separation channel 34A. After sufficient time for the desired material to pass through the intersection 40A, the voltage distribution is switched back to the original values to prevent additional material from the first reservoir 12A from flowing through the intersection 40A toward the separation channel 34A.

One application of such a "gated dispenser" is to inject a controlled, variable-sized plug of analyte from the first reservoir 12A for electrophoretic or chromatographic separation in the separation channel 34A. In such a system, the first reservoir 12A stores analyte, the second reservoir 16A stores an ionic buffer, the third reservoir 18A is a first waste reservoir and the fourth reservoir 20A is a second waste reservoir. To inject a small variable plug of analyte from the first reservoir 12A, the potentials at the buffer and first waste reservoirs 16A, 18A are simply floated for a short period of time (≈100 ms) to allow the analyte to migrate down the separation column 34A. To break off the injection plug, the potentials at the buffer reservoir 16A and the first waste reservoir 18A are reapplied. Alternatively, the valving sequence could be effected by bringing reservoirs 16A and 18A to the potential of the intersection 40A and then returning them to their original potentials. A shortfall of this method is that the composition of the injected plug has an electrophoretic mobility bias whereby the faster migrating compounds are introduced preferentially into the separation column 34A over slower migrating compounds.

Figure 5A:
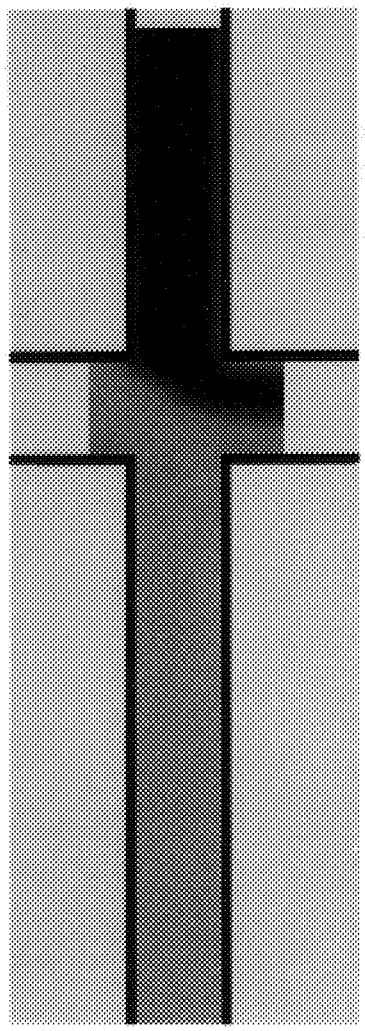
FIG. 5 are CCD images of a plug of analyte moving through the intersection of the FIG. 30 embodiment.
Figure 5B:
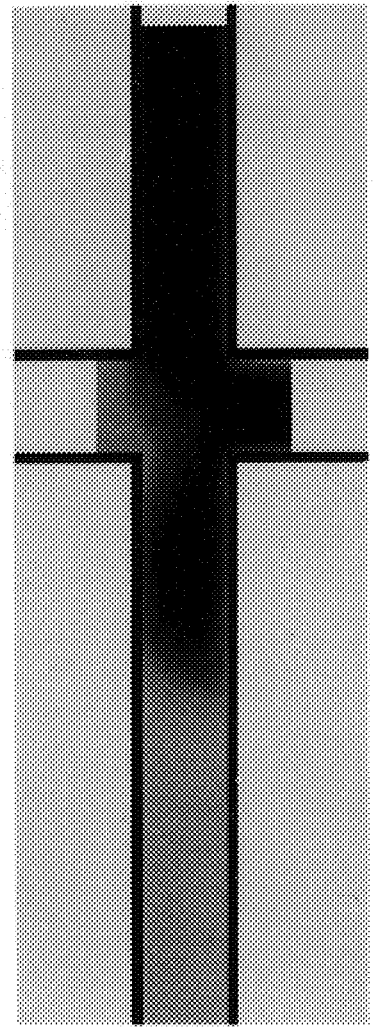
Figure 5C:
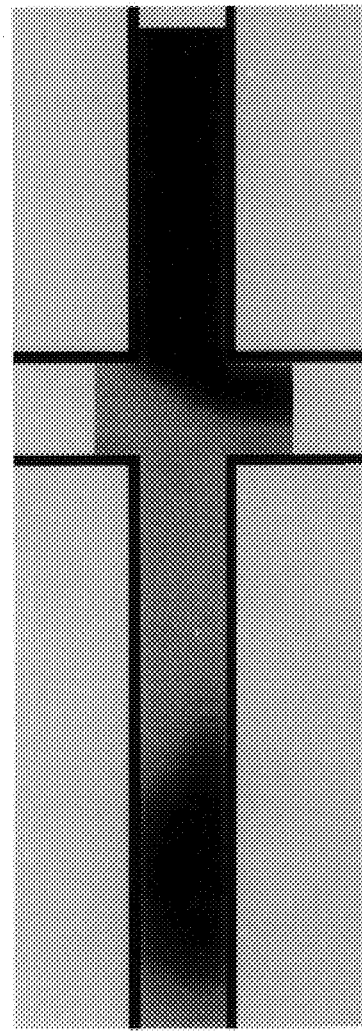

In FIG. 5, a sequential view of a plug of analyte moving through the intersection of the FIG. 3 embodiment can be seen by CCD images. The analyte being pumped through the laboratory system 10A was rhodamine B (shaded area), and the orientation of the CCD images of the injection cross or intersection is the same as in FIG. 3. The first image, (A), shows the analyte being pumped through the injection cross or intersection toward the first waste reservoir 18A prior to the injection. The second image, (B), shows the analyte plug being injected into the separation column 34A. The third image, (C), depicts the analyte plug moving away from the injection intersection after an injection plug has been completely introduced into the separation column 34A. The potentials at the buffer and first waste reservoirs 16A, 18A were floated for 100 ms while the sample moved into the separation column 34A. By the time of the (C) image, the closed gate mode has resumed to stop further analyte from moving through the intersection 40A into the separation column 34A, and a clean injection plug with a length of 142 µm has been introduced into the separation column. As discussed below, the gated injector contributes to only a minor fraction of the total plate height. The injection plug length (volume) is a function of the time of the injection and the electric field strength in the column. The shape of the injected plug is skewed slightly because of the directionality of the cleaving buffer flow. However, for a given injection period, the reproducibility of the amount injected, determined by integrating the peak area, is 1% RSD for a series of 10 replicate injections.

Electrophoresis experiments were conducted using the microchip laboratory system 10A of FIG. 3, and employed methodology according to the present invention. Chip dynamics were analyzed using analyte fluorescence. A charge coupled device (CCD) camera was used to monitor designated areas of the chip and a photomultiplier tube (PMT) tracked single point events. The CCD (Princeton Instruments, Inc. TE/CCD-512TKM camera was mounted on a stereo microscope (Nikon SMZ-U), and the laboratory system 10A was illuminated using an argon ion laser (514.5 nm, Coherent Innova 90) operating at 3 W with the beam expanded to a circular spot ≈2 cm in diameter. The PMT, with collection optics, was situated below the microchip with the optical axis perpendicular to the microchip surface. The laser was operated at approximately 20 mW, and the beam impinged upon the microchip at a 45° angle from the microchip surface and parallel to the separation channel. The laser beam and PMT observation axis were separated by a 135° angle. The point detection scheme employed a helium-neon laser (543 nm, PMS Electro-optics LHGP-0051) with an electrometer (Keithley 617) to monitor response of the PMT (Oriel 77340). The voltage controller 46 (Spellman CZE 1000R) for electrophoresis was operated between 0 and +4.4 kV relative to ground.

The type of gated injector described with respect to FIGS. 3 and 4 show electrophoretic mobility based bias as do conventional electroosmotic injections. Nonetheless, this approach has simplicity in voltage switching requirements and fabrication and provides continuous unidirectional flow through the separation channel. In addition, the gated injector provides a method for valving a variable volume of fluid into the separation channel 34A in a manner that is precisely controlled by the electrical potentials applied.

Another application of the gated dispenser 10A is to dilute or mix desired quantities of materials in a controlled manner. To implement such a mixing scheme in order to mix the materials from the first and second reservoirs 12A, 16A, the potentials in the first and second channels 26A, 30A need to be maintained higher than the potential of the intersection 40A during mixing. Such potentials will cause the materials from the first and second reservoirs 12A and 16A to simultaneously move through the intersection 40A and thereby mix the two materials. The potentials applied at the first and second reservoirs 12A, 16A can be adjusted as desired to achieve the selected concentration of each material. After dispensing the desired amounts of each material the potential at the second reservoir 16A may be increased in a manner sufficient to prevent further material from the first reservoir 12A from being transported through the intersection 40A toward the third reservoir 30A.

Analyte Injector

Figure 6:
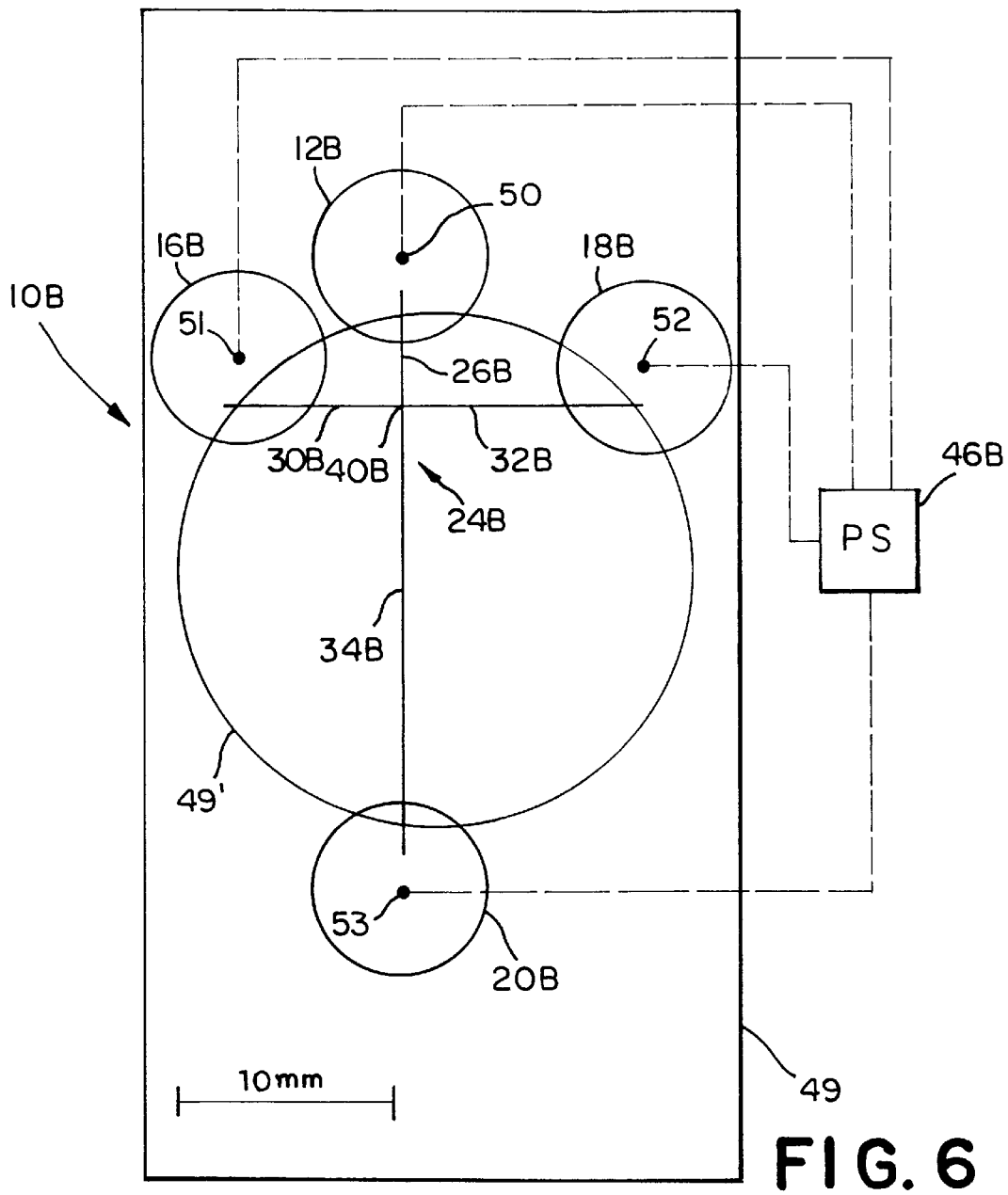
FIG. 6 is a schematic top view of a microchip laboratory system according to a third preferred embodiment of a microchip according to the present invention.

Shown in FIG. 6 is a microchip analyte injector 10B according to the a present invention. The channel pattern 24B has four distinct channels 26B, 30B, 32B, and 34B micromachined into a substrate 49 as discussed above. Each channel has an accompanying reservoir mounted above the terminus of each channel portion, and all four channels intersect at one end in a four way intersection 40B. The opposite ends of each section provide termini that extend just beyond the peripheral edge of a cover plate 49' mounted on the substrate 49. The analyte injector 10B shown in FIG. 6 is substantially identical to the gated dispenser 10A except that the electrical potentials are applied in a manner that injects a volume of material from reservoir 16% through the intersection 40B rather than from the reservoir 12B and the volume of material injected is controlled by the size of the intersection.

The embodiment shown in FIG. 6 can be used for various material manipulations. In one application, the laboratory system is used to inject an analyte from an analyte reservoir 16B through the intersection 40B for separation in the separation channel 34B. The analyte injector 10B can be operated in either "load" mode or a "run" mode. Reservoir 16B is supplied with an analyte and reservoir 12B with buffer. Reservoir 18B acts as an analyte waste reservoir, and reservoir 20B acts as a waste reservoir.

In the "load" mode, at least two types of analyte introduction are possible. In the first, known as a "floating" loading, a potential is applied to the analyte reservoir 16B with reservoir 18B grounded. At the same time, reservoirs 12B and 20B are floating, meaning that they are neither coupled to the power source, nor grounded.

The second load mode is "pinched" loading mode, wherein potentials are simultaneously applied at reservoirs 12B, 16B, and 20B, with reservoir 18B grounded in order to control the injection plug shape as discussed in more detail below. As used herein, simultaneously controlling electrical potentials at plural reservoirs means that the electrodes are connected to a operating power source at the same chemically significant time period. Floating a reservoir means disconnecting the electrode in the reservoir from the power source and thus the electrical potential at the reservoir is not controlled.

In the "run" mode, a potential is applied to the buffer reservoir 12B with reservoir 20B grounded and with reservoirs 16B and 18B at approximately half of the potential of reservoir 12B. During the run mode, the relatively high potential applied to the buffer reservoir 12B causes the analyte in the intersection 40B to move toward the waste reservoir 20B in the separation column 34B.

Diagnostic experiments were performed using rhodamine B and sulforhodamine 101 (Exciton Chemical Co., Inc.) as the analyte at 60 $\mu$M for the CCD images and 6 $\mu$M for the point detection. A sodium tetraborate buffer (50 mM, pH 9.2) was the mobile phase in the experiments. An injection of spatially well defined small volume (≈100 pL) and of small longitudinal extent ≈100 $\mu$m), injection is beneficial when performing these types of analyses.

Figure 7:
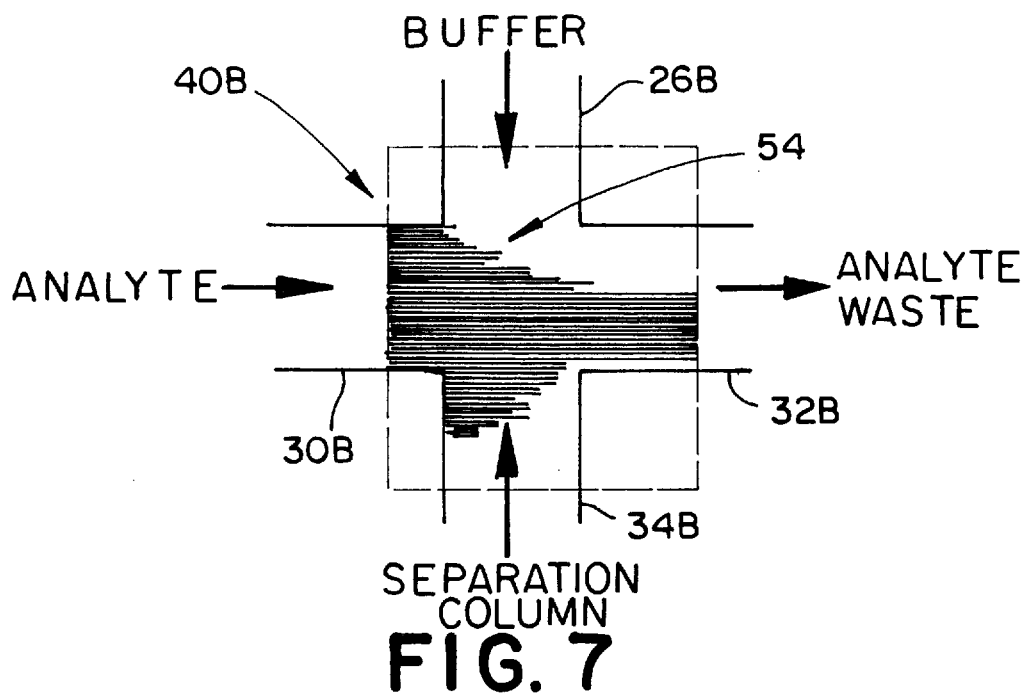
FIG. 7 is a CCD image of "sample loading mode for rhodamine B" (shaded area)

The analyte is loaded into the injection cross as a frontal electropherogram, and once the front of the slowest analyte component passes through the injection cross or intersection 40B, the analyte is ready to be analyzed. In FIG. 7, a CCD image (the area of which is denoted by the broken line square) displays the flow pattern of the analyte 54 (shaded area) and the buffer (white area) through the region of the injection intersection 40B.

By pinching the flow of the analyte, the volume of the analyte plug is stable over time. The slight asymmetry of the plug shape is due to the different electric field strengths in the buffer channel 26B (470 V/cm) and the separation channel 34B (100 V/cm) when 1.0 kV is applied to the buffer, the analyte and the waste reservoirs, and the analyte waste reservoir is grounded. However, the different field strengths do not influence the stability of the analyte plug injected. Ideally, when the analyte plug is injected into the separation channel 34B, only the analyte in the injection cross or intersection 40B would migrate into the separation channel.

The volume of the injection plug in the injection cross is approximately 120 pL with a plug length of 130 $\mu$m. A portion of the analyte 54 in the analyte channel 30B and the analyte waste channel 32B is drawn into the separation channel 34B. Following the switch to the separation (run) mode, the volume of the injection plug is approximately 250 pL with a plug length of 208 $\mu$m. These dimensions are estimated from a series of CCD images taken immediately after the switch is made to the separation mode.

Figure 8A:
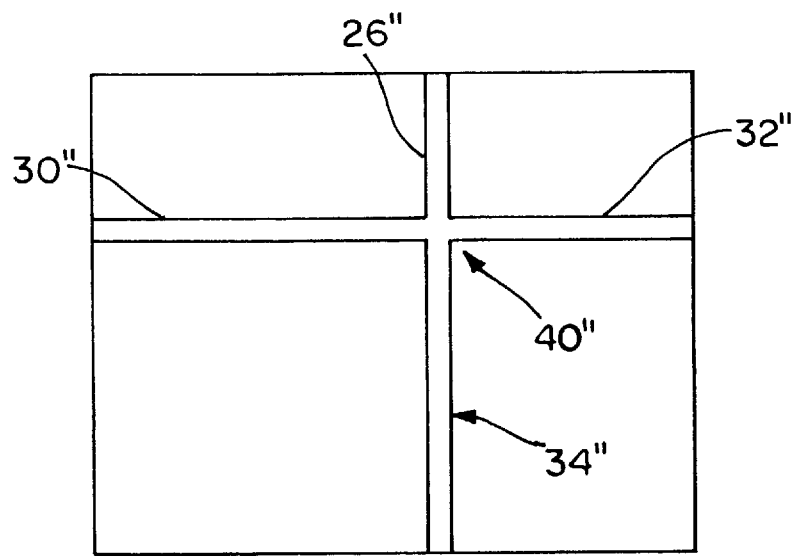
FIG. 8(a) is a schematic view of the intersection area of the microchip of FIG. 6, prior to analyte injection.
Figure 8B:
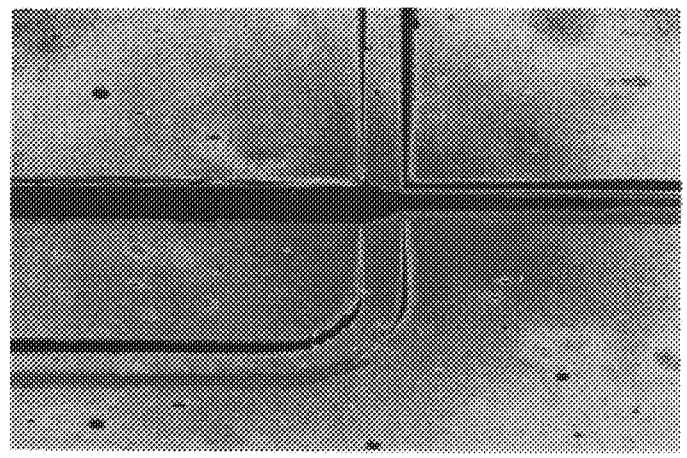
FIG. 8(b) is a CCD fluorescence image taken of the same area depicted in FIG. 8(a), after sample loading in the pinched mode.
Figure 8C:
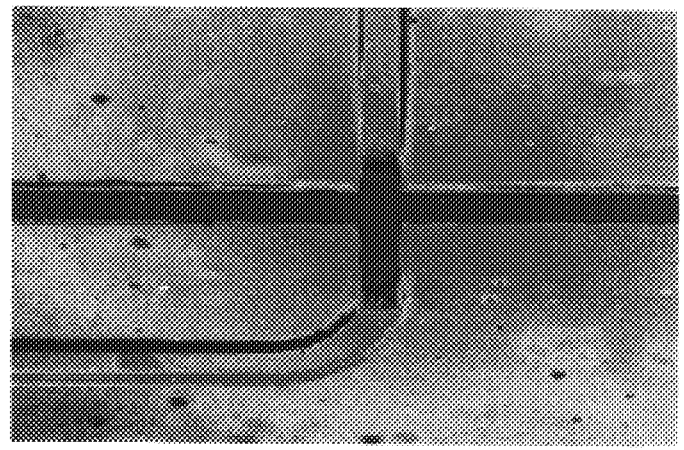
FIG. 8(c) is a photomicrograph taken of the same area depicted in FIG. 8(a), after sample loading in the floating mode.

The two modes of loading were tested for the analyte introduction into the separation channel 34B. The analyte was placed in the analyte reservoir 16B, and in both injection schemes was "transported" in the direction of reservoir 18B, a waste reservoir. CCD images of the two types of injections are depicted in FIGS. 8(a)–8(c). FIG. 8(a) schematically shows the intersection 40B, as well as the end portions of channels.

The CCD image of FIG. 8(b) is of loading in the pinched mode, just prior to being switched to the run mode. In the pinched mode, analyte (shown as white against the dark background) is pumped electrophoretically and electroosmotically from reservoir 16B to reservoir 18B (left to right) with buffer from the buffer reservoir 12B (top) and the waste reservoir 20B (bottom) traveling toward reservoir 18B (right). The voltages applied to reservoirs 12B, 16B, 18B, and 20B were 90% 90%, 0, and 100%, respectively, of the power supply output which correspond to electric field strengths in the corresponding channels of 400, 270, 690 and 20 V/cm, respectively. Although the voltage applied to the waste reservoir 20B is higher than voltage applied to the analyte reservoir 18B, the additional length of the separation channel 34B compared to the analyte channel 30B provides additional electrical resistance, and thus the flow from the analyte buffer 16B into the intersection predominates. Consequently, the analyte in the injection cross or intersection 40B has a trapezoidal shape and is spatially constricted in the channel 32B by this material transport pattern.

FIG. 8(c) shows a floating mode loading. The analyte is pumped from reservoir 16B to 18B as in the pinched injection except no potential is applied to reservoirs 12B and 20B. By not controlling the flow of mobile phase (buffer) in channel portions 26B and 34B, the analyte is free to expand into these channels through convective and diffusive flow, thereby resulting in an extended injection plug.

When comparing the pinched and floating infections, the pinched injection is superior in three areas: temporal stability of the injected volume, the precision of the injected volume, and plug length. When two or more analytes with vastly different mobilities are to be analyzed, an injection with temporal stability insures that equal volumes of the faster and slower moving analytes are introduced into the separation column or channel 34B. The high reproducibility of the injection volume facilitates the ability to perform quantitative analysis. A smaller plug length leads to a higher separation efficiency and, consequently, to a greater component capacity for a given instrument and to higher speed separations.

Figure 9:
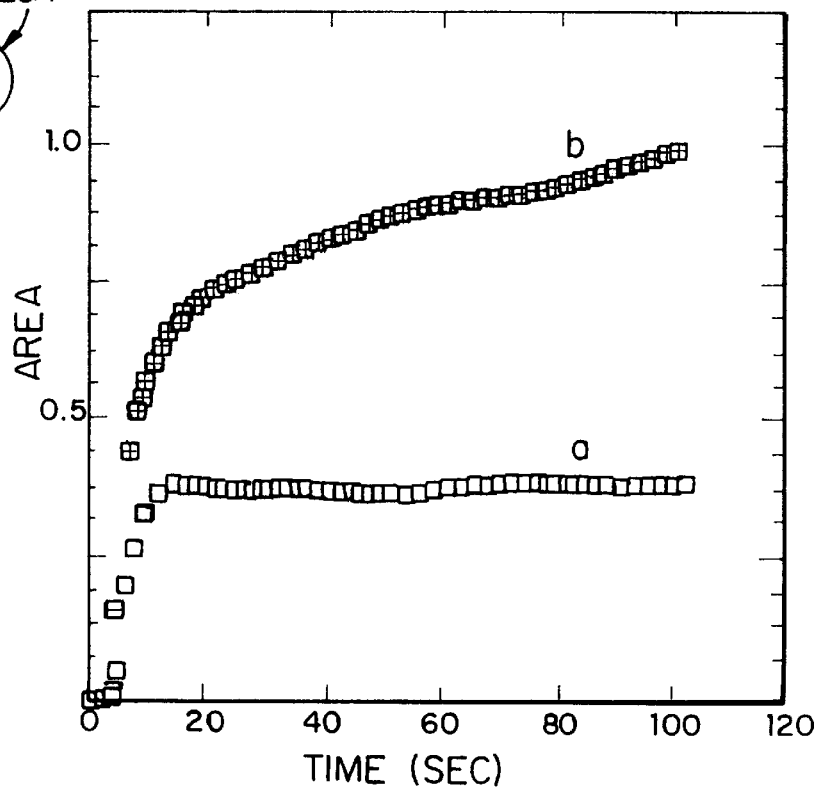
FIG. 9 shows integrated fluorescence signals for injected volume plotted versus time for pinched and floating injections.

To determine the temporal stability of each mode, a series of CCD fluorescence images were collected at 1.5 second intervals starting just prior to the analyte reaching the injection intersection 40B. An estimate of the amount of analyte that is injected was determined by integrating the fluorescence in the intersection 40B and channels 26B and 34B. This fluorescence is plotted versus time in FIG. 9.

For the pinched injection, the injected volume stabilizes in a few seconds and has a stability of 1% relative standard deviation (RSD), which is comparable to the stability of the illuminating laser. For the floating injection, the amount of analyte to be injected into the separation channel 34B increases with time because of the dispersive flow of analyte into channels 26B and 34B. For a 30 second injection, the volume of the injection plug is ca. 90 pL and stable for the pinched injection versus ca. 300 pL and continuously increasing with time for a floating injection.

By monitoring the separation channel at a point 0.9 cm from the intersection 40B, the reproducibility for the pinched injection mode was tested by integrating the area of the band profile following introduction into the separation channel 34B. For six injections with a duration of 40 seconds, the reproducibility for the pinched injection is 0.7% RSD. Most of this measured instability is from the optical measurement system. The pinched injection has a higher reproducibility because of the temporal stability of the volume injected. With electronically controlled voltage switching, the RSD is expected to improve for both schemes.

The injection plug width and, ultimately, the resolution between analytes depends largely on both the flow pattern of the analyte and the dimensions of the injection cross or intersection 40B. For this column, the width of the channel at the top is 90 $\mu$m but a channel width of 10 $\mu$m is feasible which would lead to a decrease in the volume of the injection plug from 90 pL down to 1 pL with a pinched injection.

There are situations where it may not be desirable to reverse the flow in the separation channel as described above for the "pinched" and "floating" injection schemes. Examples of such cases might be the injection of a new sample plug before the preceding plug has been completely eluted or the use of a post-column reactor where reagent is continuously being injected into the end of the separation column. In the latter case, it would in general not be desirable to have the reagent flowing back up into the separation channel.

Alternate Analyte Injector

Figure 10:
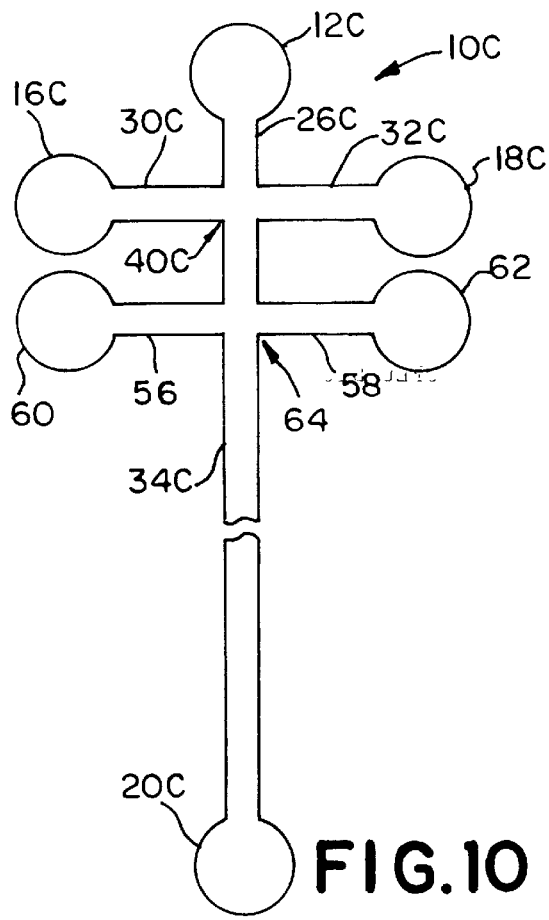
FIG. 10 is a schematic, top view of a microchip according to a fourth preferred embodiment of the present invention.

FIG. 10 illustrates an alternate analyte injector system 10C having six different ports or channels 26C, 30C, 32C, 34C, 56, and 58 respectively connected to six different reservoirs 12C, 16C, 18C, 20C, 60, and 62. The letter C after each element number indicates that the indicated element is analogous to a correspondingly numbered elements of FIG. 1. The microchip laboratory system 10C is similar to laboratory systems 10, 10A, and 10B described previously, in that an injection cross or intersection 40C is provided. In the FIG. 10 embodiment, a second intersection 64 and two additional reservoirs 60 and 62 are also provided to overcome the problems with reversing the flow in the separation channel.

Like the previous embodiments, the analyte injector system 10C can be used to implement an analyte separation by electrophoresis or chromatography or dispense material into some other processing element. In the laboratory system 10C, the reservoir 12C contains separating buffer, reservoir 16C contains the analyte, and reservoirs 18C and 20C are waste reservoirs. Intersection 40C preferably is operated in the pinched mode as in the embodiment shown in FIG. 6. The lower intersection 64, in fluid communication with reservoirs 60 and 62, are used to provide additional flow so that a continuous buffer stream can be directed down towards the waste reservoir 20C and, when needed, upwards toward the injection intersection 40C. Reservoir 60 and attached channel 56 are not necessary, although they improve performance by reducing band broadening as a plug passes the lower intersection 64. In many cases, the flow from reservoir 60 will be symmetric with that from reservoir 62.

Figure 11:
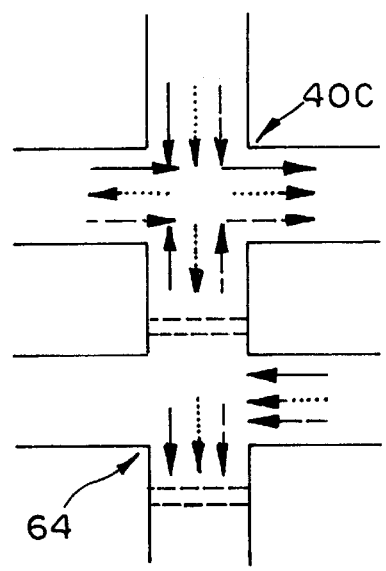
FIG. 11 is an enlarged view of the intersection region of FIG. 10.

FIG. 11 is an enlarged view of the two intersections 40C and 64. The different types of arrows show the flow directions at given instances in time for injection of a plug of analyte into the separation channel. The solid arrows show the initial flow pattern where the analyte is electrokinetically pumped into the upper intersection 40C and "pinched" by material flow from reservoirs 12C, 60, and 62 toward this same intersection. Flow away from the injection intersection 40C is carried to the analyte waste reservoir 18C. The analyte is also flowing from the reservoir 16C to the analyte waste reservoir 18C. Under these conditions, flow from reservoir 60 (and reservoir 62) is also going down the separation channel 34C to the waste reservoir 20C. Such a flow pattern is created by simultaneously controlling the electrical potentials at all six reservoirs.

A plug of the analyte is injected through the injection intersection 40C into the separation channel 34C by switching to the flow profile shown by the short dashed arrows. Buffer flows down from reservoir 12C to the injection intersection 40C and towards reservoirs 16C, 18C, and 20C. This flow profile also pushes the analyte plug toward waste reservoir 20C into the separation channel 34C as described before. This flow profile is held for a sufficient length of time so as to move the analyte plug past the lower intersection 64. The flow of buffer from reservoirs 60 and 62 should be low as indicated by the short arrow and into the separation channel 34C to minimize distortion.

The distance between the upper and lower intersections 40C and 64, respectively, should be as small as possible to minimize plug distortion and criticality of timing in the switching between the two flow conditions. Electrodes for sensing the electrical potential may also be placed at the lower intersection and in the channels 56 and 58 to assist in adjusting the electrical potentials for proper flow control. Accurate flow control at the lower intersection 64 may be necessary to prevent undesired band broadening.

After the sample plug passes the lower intersection, the potentials are switched back to the initial conditions to give the original flow profile as shown with the long dashed arrows. This flow pattern will allow buffer flow into the separation channel 34C while the next analyte plug is being transported to the plug fanning region in the upper intersection 40C. This injection scheme will allow a rapid succession of injections to be made and may be very important for samples that are slow to migrate or if it takes a long time to achieve a homogeneous sample at the upper intersection 40C such as with entangled polymer solutions. This implementation of the pinched injection also maintains unidirectional flow through the separation channel as might be required for a post-column reaction as discussed below with respect to FIG. 22.

Serpentine Channel

Figure 12:
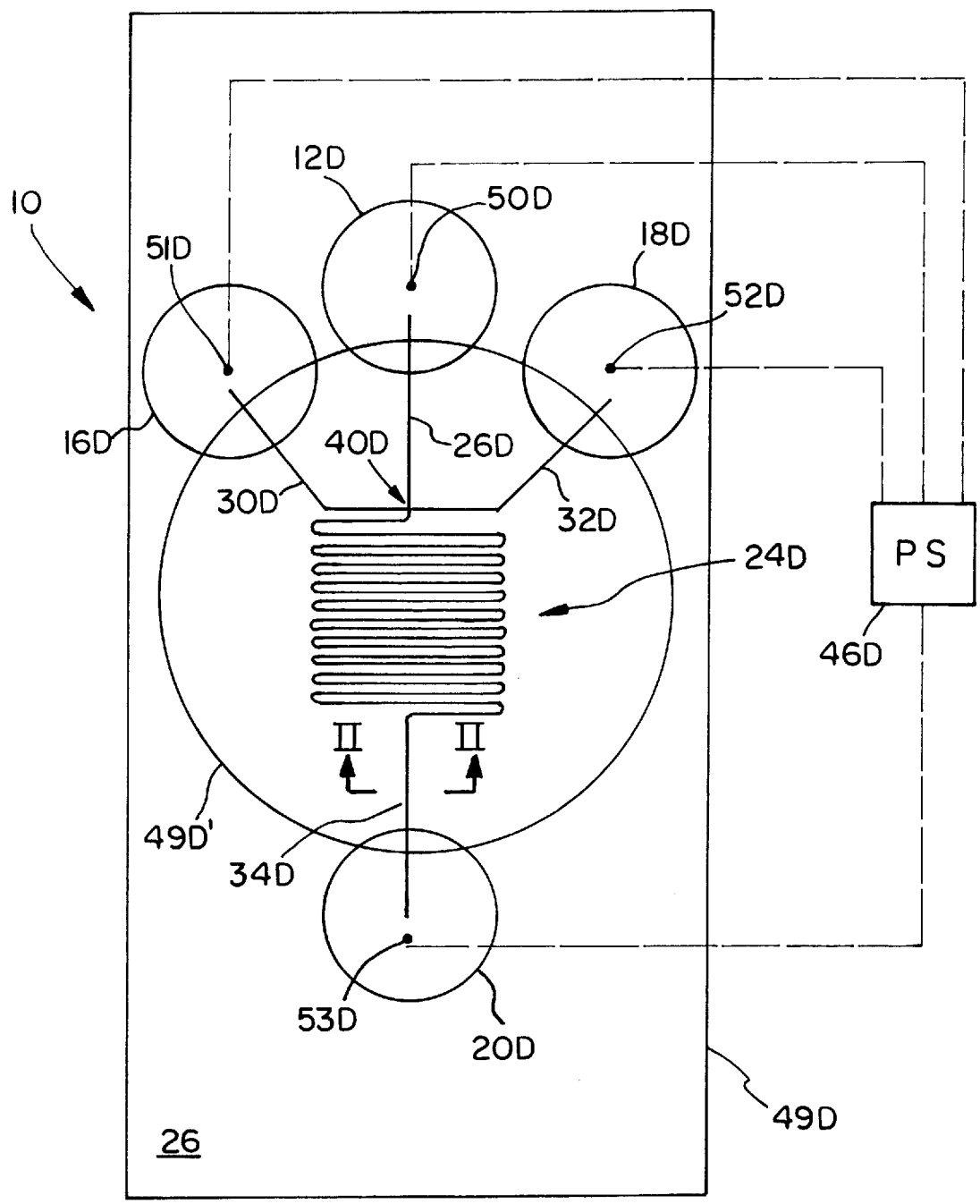
FIG. 12 is a schematic top view of a microchip laboratory system according to a fifth preferred embodiment according to the present invention.

Another embodiment of the invention is the modified analyte injector system 10D shown in FIG. 12. The laboratory system 10D shown in FIG. 12 is substantially identical to the laboratory system 10B shown in FIG. 6, except that the separation channel 34D follows a serpentine path. The serpentine path of the separation channel 34D allows the length of the separation channel to be greatly increased without substantially increasing the area of the substrate 49D needed to implement the serpentine path. Increasing the length of the separation channel 34D increases the ability of the laboratory system 10D to distinguish elements of an analyte. In one particularly preferred embodiment, the enclosed length (that which is covered by the cover plate 49D') of the channels extending from reservoir 16D to reservoir 18D is 19 mm, while the length of channel portion 26D is 6.4 mm and channel 34D is 171 mm. The turn radius of each turn of the channel 34D, which serves as a separation column, is 0.16 mm.

Figure 13A:
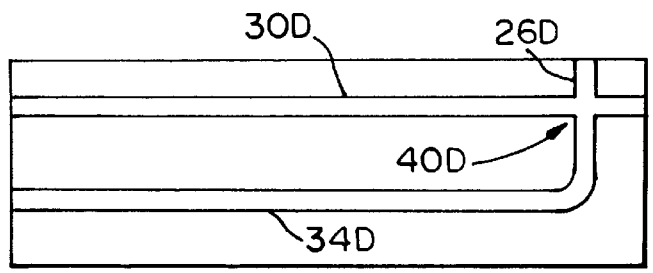
FIG. 13(a) is a schematic view of a CCD camera view of the intersection area of the microchip laboratory system of FIG. 12.

To perform a separation using the modified analyte injector system 10D, an analyte is first loaded into the injection intersection 40D using one of the loading methods described above. After the analyte has been loaded into the intersection 40D of the microchip laboratory system 10, the voltages are manually switched from the loading mode to the run (separation) mode of operation. FIGS. 13(a)–13(e) illustrate a separation of rhodamine B (less retained) and sulforhodamine (more retained) using the following conditions: $E_{inj}$=400 V/cm, $E_{run}$=150 V/cm, buffer=50 mM sodium tetaborate at pH 9.2. The CCD images demonstrate the separation process at 1 second intervals, with FIG. 13(a) showing a schematic of the section of the chip imaged, and with FIGS. 13(b)–13(e) showing the separation unfold.

Figure 13B:
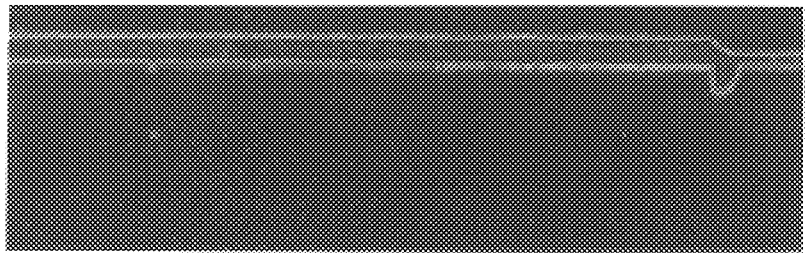
FIG. 13(b) is a CCD fluorescence image taken of the same area depicted in FIG. 13(a), after sample loading in the pinched mode.
Figure 13C:
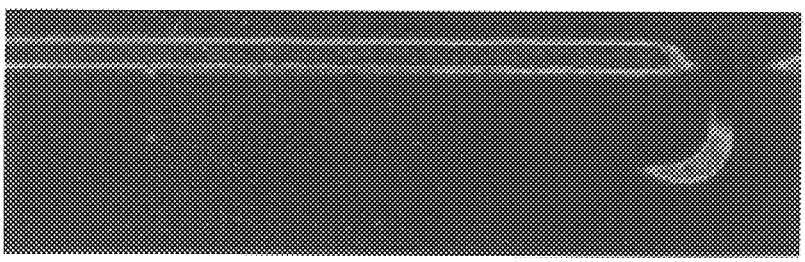
FIGS. 13(c)–13(e) are CCD fluorescence images taken of the same area depicted in FIG. 13(a), sequentially showing a plug of analyte moving away from the channel intersection at 1, 2, and 3 seconds, respectively, after switching to the run mode.
Figure 13D:
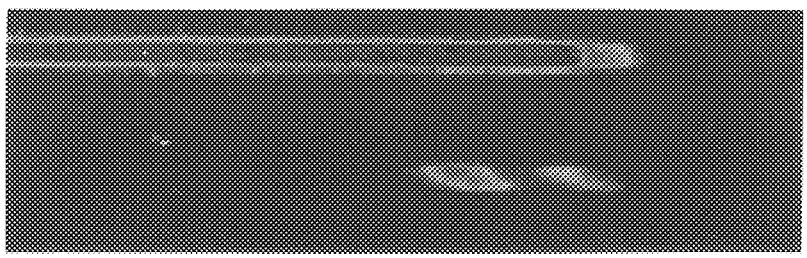
Figure 13E:
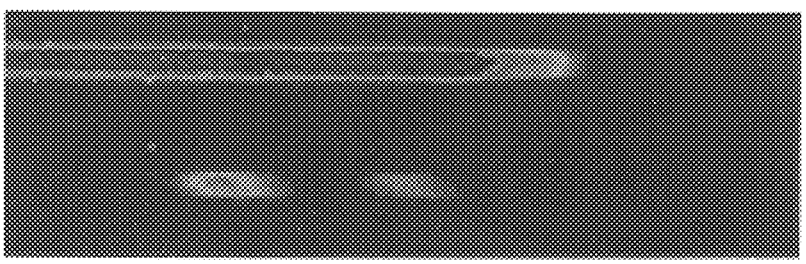

FIG. 13(b) again shows the pinched injection with the applied voltages at reservoirs 12D, 16D, and 20D equal and reservoir 18D grounded. FIGS. 13(c)–13(e) shows the plug moving away from the intersection at 1, 2, and 3 seconds, respectively, after switching to the run mode. In FIG. 13(c), the injection plug is migrating around a 90° turn, and band distortion is visible due to the inner portion of the plug traveling less distance than the outer portion. By FIG. 13(d), the analytes have separated into distinct bands, which are distorted in the shape of a parallelogram. In FIG. 13(e), the bands are well separated and have attained a more rectangular shape, i.e., collapsing of the parallelogram, due to radial diffusion, an additional contribution to efficiency loss.

When the switch is made from the load mode to the run mode, a clean break of the injection plug from the analyte stream is desired to avoid tailing. This is achieved by pumping the mobile phase or buffer from channel 26D into channels 30D, 32D, and 34D simultaneously by maintaining the potential at the intersection 40D below the potential of reservoir 12D and above the potentials of reservoirs 16D, 18D, and 20D In the representative experiments described herein, the intersection 40D was maintained at 66% of the potential of reservoir 12D during the run mode. This provided sufficient flow of the analyte back away from the injection intersection 40D down channels 30D and 32D without decreasing the field strength in the separation channel 34D significantly. Alternate channel designs would allow a greater fraction of the potential applied at reservoir 12D to be dropped across the separation channel 34D, thereby improving efficiency.

This three way flow is demonstrated in FIGS. 13(c)–13(e) as the analytes in channels 30D and 32D (left and right, respectively) move further away from the intersection with time. Three way flow permits well-defined, reproducible injections with minimal bleed of the analyte into the separation channel 34D.

Detectors

In most applications envisaged for these integrated microsystems for chemical analysis or synthesis it will be necessary to quantify the material present in a channel at one or more positions similar to conventional laboratory measurement processes. Techniques typically utilized for quantification include, but are not limited to, optical absorbance, refractive index changes, fluorescence emission, chemiluminescence, various forms of Raman spectroscopy, electrical conductometric measurements, electrochemical amperiometric measurements, acoustic wave propagation measurements.

Optical absorbence measurements are commonly employed with conventional laboratory analysis systems because of the generality of the phenomenon in the UV portion of the electromagnetic spectrum. Optical absorbance is commonly determined by measuring the attenuation of impinging optical power as it passes through a known length of material to be quantified. Alternative approaches are possible with laser technology including photo acoustic and photo thermal techniques. Such measurements can be utilized with the microchip technology discussed here with the additional advantage of potentially integrating optical wave guides on microfabricated devices. The use of solid-state optical sources such as LEDs and diode lasers with and without frequency conversion elements would be attractive for reduction of system size. Integration of solid state optical source and detector technology onto a chip does not presently appear viable but may one day be of interest.

Refractive index detectors have also been commonly used for quantification of flowing stream chemical analysis systems because of generality of the phenomenon but have typically been less sensitive than optical absorption. Laser based implementations of refractive index detection could provide adequate sensitivity in some situations and have advantages of simplicity. Fluorescence emission (or fluorescence detection) is an extremely sensitive detection technique and is commonly employed for the analysis of biological materials. This approach to detection has much relevance to miniature chemical analysis and synthesis devices because of the sensitivity of the technique and the small volumes that can be manipulated and analyzed (volumes in the picoliter range are feasible). For example, a 100 pL sample volume with 1 nM concentration of analyte would have only 60,000 analyte molecules to be processed and detected. There are several demonstrations in the literature of detecting a single molecule in solution by fluorescence detection. A laser source is often used as the excitation source for ultrasensitive measurements but conventional light sources such as rare gas discharge lamps and light emitting diodes LEDs) are also used. The fluorescence emission can be detected by a photomultiplier tube, photodiode or other light sensor. An array detector such as a charge coupled device (CCD) detector can be used to image an analyte spatial distribution.

Raman spectroscopy can be used as a detection method for microchip devices with the advantage of gaining molecular vibrational information, but with the disadvantage of relatively poor sensitivity. Sensitivity has been increased through surface enhanced Raman spectroscopy (SERS) effects but only at the research level. Electrical or electrochemical detection approaches are also of particular interest for implementation on microchip devices due to the ease of integration onto a microfabricated structure and the potentially high sensitivity that can be attained. The most general approach to electrical quantification is a conductometric measurement, i.e., a measurement of the conductivity of an ionic sample. The presence of an ionized analyte can correspondingly increase the conductivity of a fluid and thus allow quantification. Amperiometric measurements imply the measurement of the current through an electrode at a given electrical potential due to the reduction or oxidation of a molecule at the electrode. Some selectivity can be obtained by controlling the potential of the electrode but it is minimal. Amperiometric detection is a less general technique than conductivity because not all molecules can be reduced or oxidized within the limited potentials that can be used with common solvents. Sensitivities in the 1 nM range have been demonstrated in small volumes (10 nL). The other advantage of this technique is that the number of electrons measured (through the current) is equal to the number of molecules present. The electrodes required for either of these detection methods can be included on a microfabricated device through a photolithographic patterning and metal deposition process. Electrodes could also be used to initiate a chemiluminescence detection process, i.e., an excited state molecule is generated via an oxidation-reduction process which then transfers its energy to an analyte molecule, subsequently emitting a photon that is detected.

Acoustic measurements can also be used for quantification of materials but have not been widely used to date. One method that has been used primarily for gas phase detection is the attenuation or phase shift of a surface acoustic wave (SAW). Adsorption of material to the surface of a substrate where a SAW is propagating affects the propagation characteristics and allows a concentration determination. Selective sorbents on the surface of the SAW device are often used. Similar techniques may be useful in the devices described herein.

The mixing capabilities of the microchip laboratory systems described herein lend themselves to detection processes that include the addition of one or more reagents. Derivatization reactions are commonly used in biochemical assays. For example, amino acids, peptides and proteins are commonly labeled with dansylating reagents or o-phthaldialdehyde to produce fluorescent molecules that are easily detectable. Alternatively, an enzyme could be used as a labeling molecule and reagents, including substrate, could be added to provide an enzyme amplified detection scheme, i.e., the enzyme produces a detectable product. There are many examples where such an approach has been used in conventional laboratory procedures to enhance detection, either by absorbence or fluorescence. A third example of a detection method that could benefit from integrated mixing methods is chemiluminescence detection. In these types of detection scenarios, a reagent and a catalyst are mixed with an appropriate target molecule to produce an excited state molecule that emits a detectable photon.

Analyte Stacking

To enhance the sensitivity of the microchip laboratory system 10D, an analyte pre-concentration can be performed prior to the separation. Concentration enhancement is a valuable tool especially when analyzing environmental samples and biological materials, two areas targeted by microchip technology. Analyte stacking is a convenient technique to incorporate with electrophoretic analyses. To employ analyte stacking, the analyte is prepared in a buffer with a lower conductivity than the separation buffer. The difference in conductivity causes the ions in the analyte to stack at the beginning or end of the analyte plug, thereby resulting in a concentrated analyte plug portion that is detected more easily. More elaborate preconcentration techniques include two and three buffer systems, i.e., transient isotachophoretic preconcentration. It will be evident that the greater the number of solutions involved, the more difficult the injection technique is to implement. Pre-concentration steps are well suited for implementation on a microchip. Electroosmotically driven flow enables separation and sample buffers to be controlled without the use of valves or pumps. Low dead volume connections between channels can be easily fabricated enabling fluid manipulation with high precision, speed and reproducibility.

Referring again to FIG. 12, the pre-concentration of the analyte is performed at the top of the separation channel 34D using a modified gated injection to stack the analyte. First, an analyte plug is introduced onto the separation channel 34D using electroosmotic flow. The analyte plug is then followed by more separation buffer from the buffer reservoir 16D. At this point, the analyte stacks at the boundaries of the analyte and separation buffers. Dansylated amino acids were used as the analyte, which are anions that stack at the rear boundary of the analyte buffer plug. Implementation of the analyte stacking is described along with the effects of the stacking on both the separation efficiency and detection limits.

To employ a gated injection using the microchip laboratory system 10D, the analyte is stored in the top reservoir 12D and the buffer is stored in the left reservoir 16D. The gated injection used for the analyte stacking is performed, on an analyte having an ionic strength that is less than that of the running buffer. Buffer is transported by electroosmosis from the buffer reservoir 16D towards both the analyte waste and waste reservoirs 18D, 20D. This buffer stream prevents the analyte from bleeding into the separation channel 34D. Within a representative embodiment, the relative potentials at the buffer, analyte, analyte waste and waste reservoirs are 1, 0.9, 0.7 and 0, respectively. For 1 kV applied to the microchip, the field strengths in the buffer, analyte, analyte waste, and separation channels during the separation are 170, 130, 180, and 120 V/cm, respectively.

To inject the analyte onto the separation channel 34D, the potential at the buffer reservoir 16D is floated (opening of the high voltage switch) for a brief period of time (0.1 to 10 s), and analyte migrates into the separation channel. For 1 kV applied to the microchip, the field strengths in the buffer, sample, sample waste, and separation channels during the injection are 0, 240, 120, and 110 V/cm, respectively. To break off the analyte plug, the potential at the buffer reservoir 16D is reapplied (closing of a high voltage switch). The volume of the analyte plug is a function of the injection time, electric field strength, and electrophoretic mobility.

Figure 14:
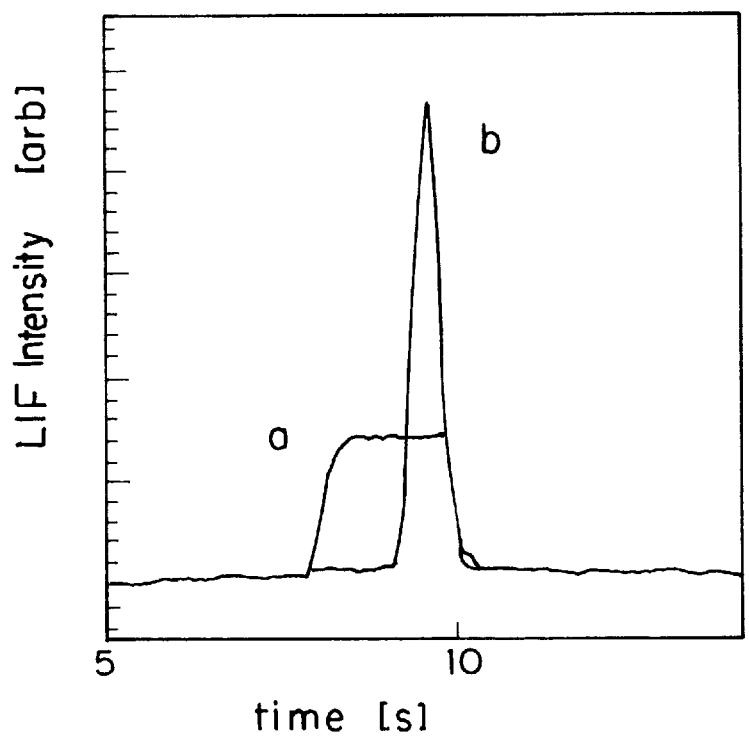
FIG. 14 shows two injection profiles for didansyl-lysine injected for 2s with γ equal to 0.97 and 9.7.

The separation buffer and analyte compositions can be quite different, yet with the gated injections the integrity of both the analyte and buffer streams can be alternately maintained in the separation channel 34D to perform the stacking operation. The analyte stacking depends on the relative conductivity of the separation buffer to analyte, $\gamma$. For example, with a 5 mM separation buffer and a 0.516 mM sample (0.016 mM dansyl-lysine and 0.5 mM sample buffer), $\gamma$ is equal to 9.7. FIG. 14 shows two injection profiles for didansyl-lysine injected for 2 s with $\gamma$ equal to 0.97 and 9.7. The injection profile with $\gamma$=0.97 (the separation and sample buffers are both 5 mM) shows no stacking. The second profile with $\gamma$=9.7 shows a modest enhancement of 3.5 for relative peak heights over the injection with $\gamma$=0.97. Didansyl-lysine is an anion, and thus stacks at the rear boundary of the sample buffer plug. In addition to increasing the analyte concentration, the spatial extent of the plug is confined. The injection profile with $\gamma$=9.7 has a width at half-height of 0.41 s, while the injection profile with $\gamma$=0.97 has a width at half-height of 1.88 s. The electric field strength in the separation channel 34D during the injection (injection field strength) is 95% of the electric field strength in the separation channel during the separation (separation field strength). These profiles are measured while the separation field strength is applied. For an injection time of 2 s, an injection plug width of 1.9 s is expected for $\gamma$=0.97.

The concentration enhancement due to stacking was evaluated for several sample plug lengths and relative conductivities of the separation buffer and analyte. The enhancement due to stacking increases with increasing relative conductivities, $\gamma$. In Table 1, the enhancement is listed for g from 0.97 to 970. Although the enhancement is largest when $\gamma$=970, the separation efficiency suffers due to an electroosmotic pressure originating at the concentration boundary when the relative conductivity is too large. A compromise between the stacking enhancement and separation efficiency must be reached and $\gamma$=10 has been found to be optimal. For separations performed using stacked injections with $\gamma$=97 and 970, didansyl-lysine and dansyl-isoleucine could not be resolved due to a loss in efficiency. Also, because the injection process on the microchip is computer controlled, and the column is not physically transported from vial to vial, the reproducibility of the stacked injections is 2.1% rsd (percent relative standard deviation) for peak area for 6 replicate analyses. For comparison, the non-stacked, gated injection has a 1.4% rsd for peak area for 6 replicate analyses, and the pinched injection has a 0.75% rsd for peak area for 6 replicate analyses. These correspond well to reported values for large-scale, commercial, automated capillary electrophoresis instruments. However, injections made on the microchip are ≈100 times smaller in volume, e.g. 100 pL on the microchip versus 10 nL on a commercial instrument.

TABLE 1

Variation of stacking enhancement with relative conductivity, $\gamma$.

| $\gamma$ | Concentration Enhancement |
|---|---|
| 0.97 | 1 |
| 9.7 | 6.5 |
| 97 | 11.5 |
| 970 | 13.8 |

Buffer streams of different conductivities can be accurately combined on microchips. Described herein is a simple stacking method, although more elaborate stacking schemes can be employed by fabricating a microchip with additional buffer reservoirs. In addition, the leading and trailing electrolyte buffers can be selected to enhance the sample stacking, and ultimately, to lower the detection limits beyond that demonstrated here. It is also noted that much larger enhancements are expected for inorganic (elemental) cations due to the combination of field amplified analyte injection and better matching of analyte and buffer ion mobilities.

Figure 15:
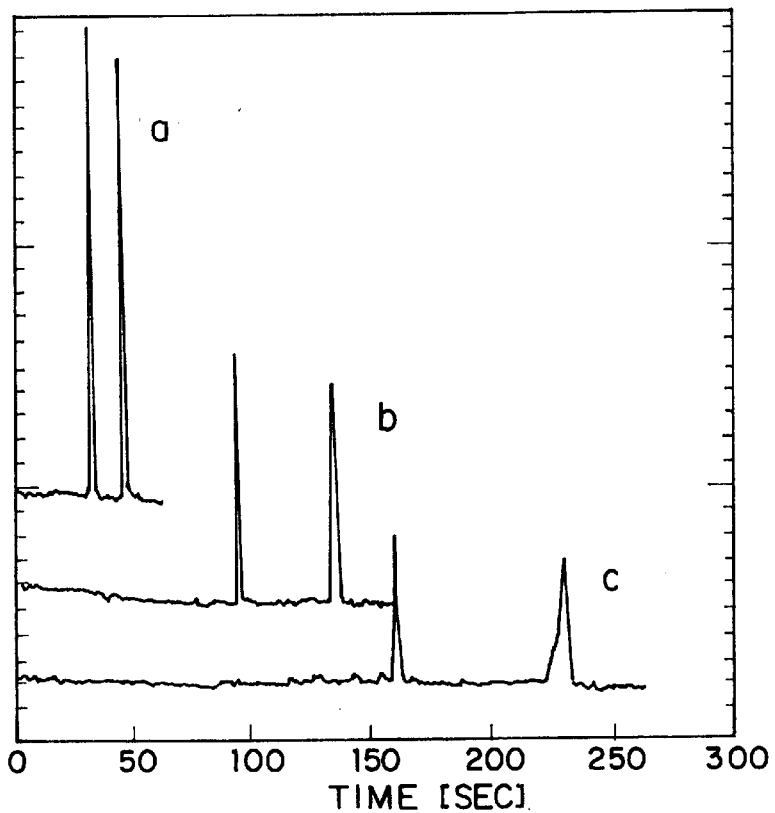
FIG. 15 are electropherograms taken at (a) 3.3 cm, (b) 9.9 cm, and (c) 16.5 cm from the point of injection for rhodamine B (less retained) and sulforhodamine (more retained)

Regardless of whether sample stacking is used, the microchip laboratory system 10D of FIG. 12 can be employed to achieve electrophoretic separation of an analyte composed of rhodamine B and sulforhodamine. FIG. 15 are electropherograms at (a) 3.3 cm, (b) 9.9 cm, and (c) 16.5 cm from the point of injection for rhodamine B (less retained) and sulforhodamine (more retained). These were taken using the following conditions: injection type was pinched, $E_{inj}$=500 V/cm, $E_{run}$170 V/cm, buffer=50 mM sodium tetraborate at pH 9.2. To obtain electropherograms in the conventional manner, single point detection with the helium-neon laser (green line) was used at different locations down the axis of the separation channel 34D.

An important measure of the utility of a separation system is the number of plates generated per unit time, as given by the formula $N/t = L/(Ht)$ where N is the number of theoretical plates, t is the separation time, L is the length of the separation column, and H is the height equivalent to a theoretical plate. The plate height, H, can be written as $H = A + B/u$ where A is the sum of the contributions from the injection plug length and the detector path length, B is equal to $2D_m$, where $D_m$ is the diffusion coefficient for the analyte in the buffer, and u is the linear velocity of the analyte.

Combining the two equations above and substituting $u = \mu E$ where $\mu$ is the effective electrophoretic mobility of the analyte and E is the electric field strength, the plates per unit time can be expressed as a function of the electric field strength:

$N/t = (\mu E)^2 / (A\mu E + B)$

At low electric field strengths when axial diffusion is the dominant form of band dispersion, the term $A\mu E$ is small relative to B and consequently, the number of plates per second increases with the square of the electric field strength.

As the electric field strength increases, the plate height approaches a constant value, and the plates per unit time increases linearly with the electric field strength because B is small relative to $A\mu E$. It is thus advantageous to have A as small as possible, a benefit of the pinched injection scheme.

Figure 16:
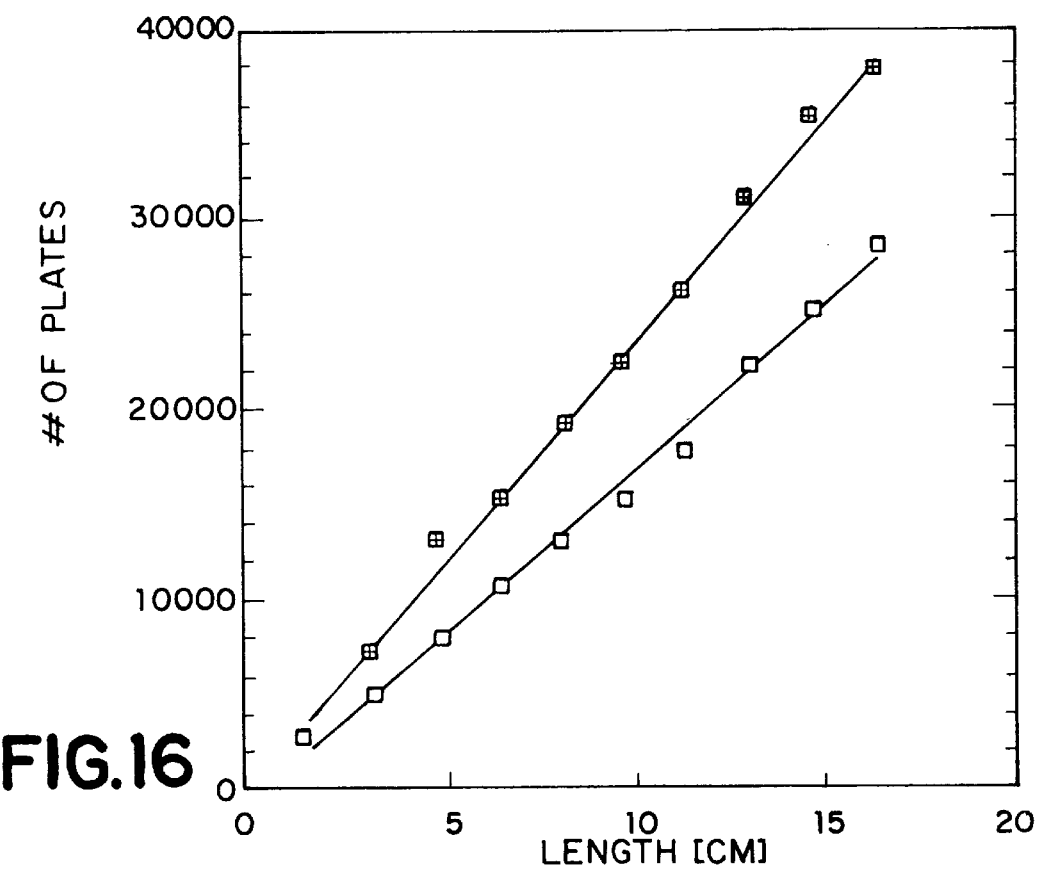
FIG. 16 is a plot of the efficiency data generated from the electropherograms of FIG. 15, showing variation of the plate number with channel length for rhodamine B (square with plus) and sulforhodamine (square with plus) and sulforhodamine (square with dot) with best linear fit (solid lines) for each analyte.

The efficiency of the electrophoretic separation of rhodamine B and sulforhodamine at ten evenly spaced positions was monitored, each constituting a separate experiment. At 16.5 cm from the point of injection, the efficiencies of rhodamine B and sulforhodamine are 38,100 and 29,000 plates, respectively. Efficiencies of this magnitude are sufficient for many separation applications. The linearity of the data provides information about the uniformity and quality of the channel along its length. If a defect in the channel, e.g., a large pit, was present a sharp decrease in the efficiency would result; however, none was detected. The efficiency data are plotted in FIG. 16 (conditions for FIG. 16 were the same as for FIG. 15).

A similar separation experiment was performed using the microchip analyte injector 10B of FIG. 6. Because of the straight separation channel 34B, the analyte injector 10B enables faster separations than are possible using the serpentine separation channel 34D of the alternate analyte injector 10D shown in FIG. 12. In addition, the electric field strengths used were higher (470 V/cm and 100 V/cm for the buffer and separation channels 26B, 34B, respectively), which further increased the speed of the separations.

Figure 17A:
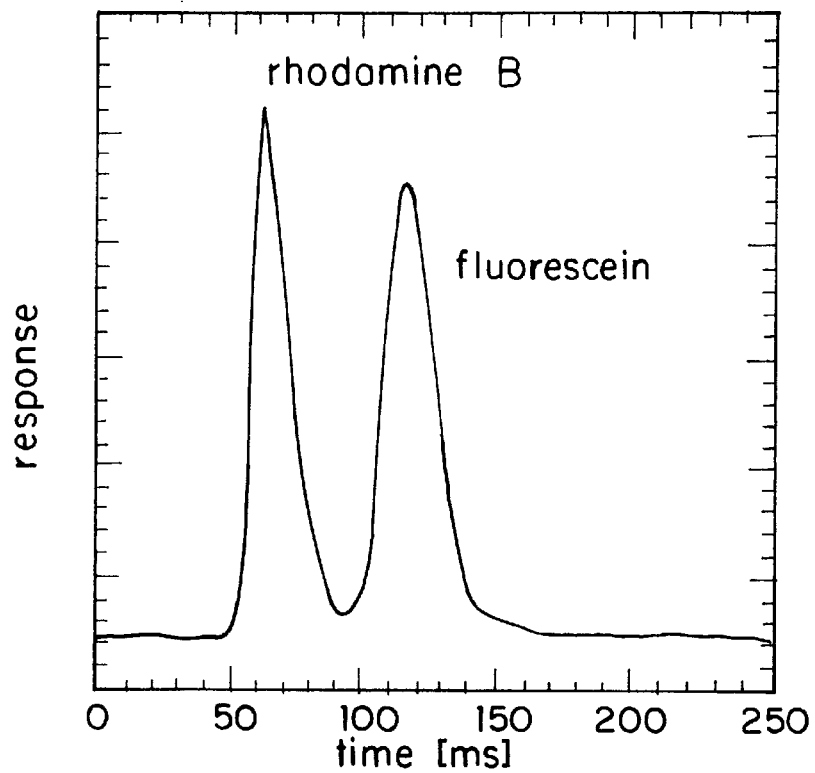
FIG. 17(a) is an electropherogram of rhodamine B and fluorescein with a separation field strength of 1.5 kV/cm and a separation length of 0.9 mm.
Figure 17B:
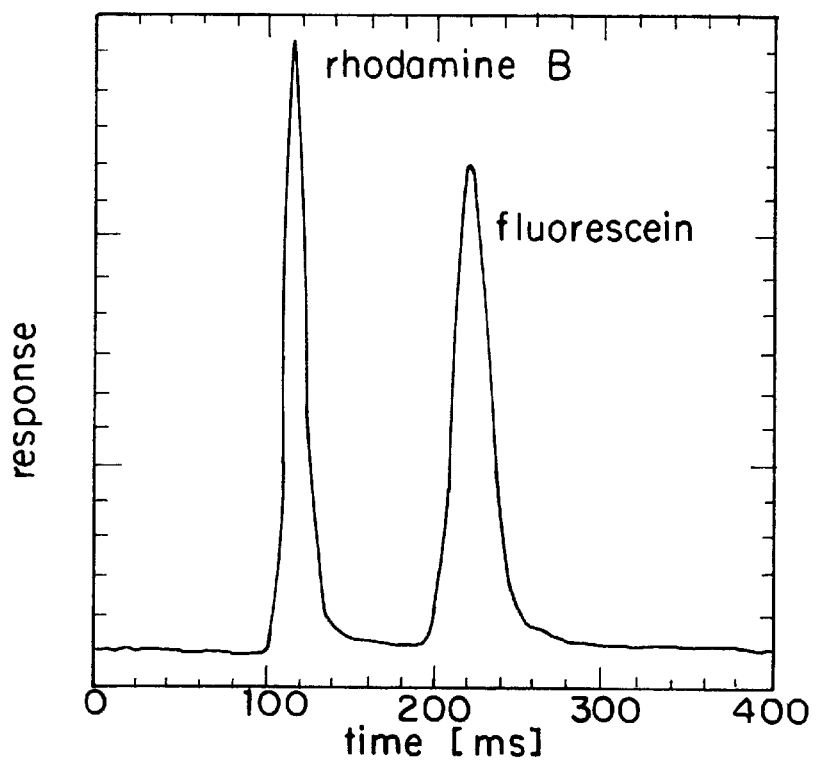
FIG. 17(b) is an electropherogram of rhodamine B and fluorescein with a separation field strength of 1.5 kV/cm and a separation length of 1.6 mm.
Figure 17C:
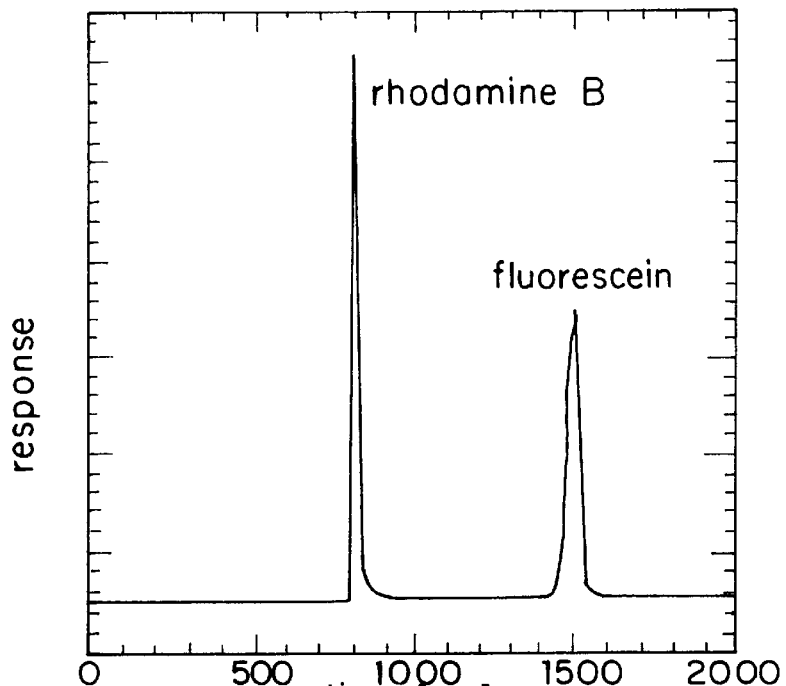
FIG. 17(c) is an electropherogram of rhodamine B and fluorescein with a separation field strength of 1.5 kV/cm and a separation length of 11.1 mm.

One particular advantage to the planar microchip laboratory system 10B of the present invention is that with laser induced fluorescence the point of detection can be placed anywhere along the separation column. The electropherograms are detected at separation length of 0.9 mm, 1.6 mm and 11.1 mm from the injection intersection 40B. The 1.6 mm and 11.1 mm separation lengths were used over a range of electric field strengths from 0.06 to 1.5 kV/cm, and the separations had baseline resolution over this range. At an electric field strength of 1.5 kV/cm, the analytes, rhodamine B and fluorescein, are resolved in less than 150 ms for the 0.9 mm separation length, as shown in FIG. 17(a), in less than 260 ms for the 1.6 mm separation length, as shown in FIG. 17(b), and in less than 1.6 seconds for the 11.1 mm separation length, as shown in FIG. 17(c).

Due to the trapezoidal geometry of the channels, the upper corners make it difficult to cut the sample plug away precisely when the potentials are switched from the sample loading mode to the separation mode. Thus, the injection plug has a slight tail associated with it, and this effect probably accounts for the tailing observed in the separated peaks.

Figure 18:
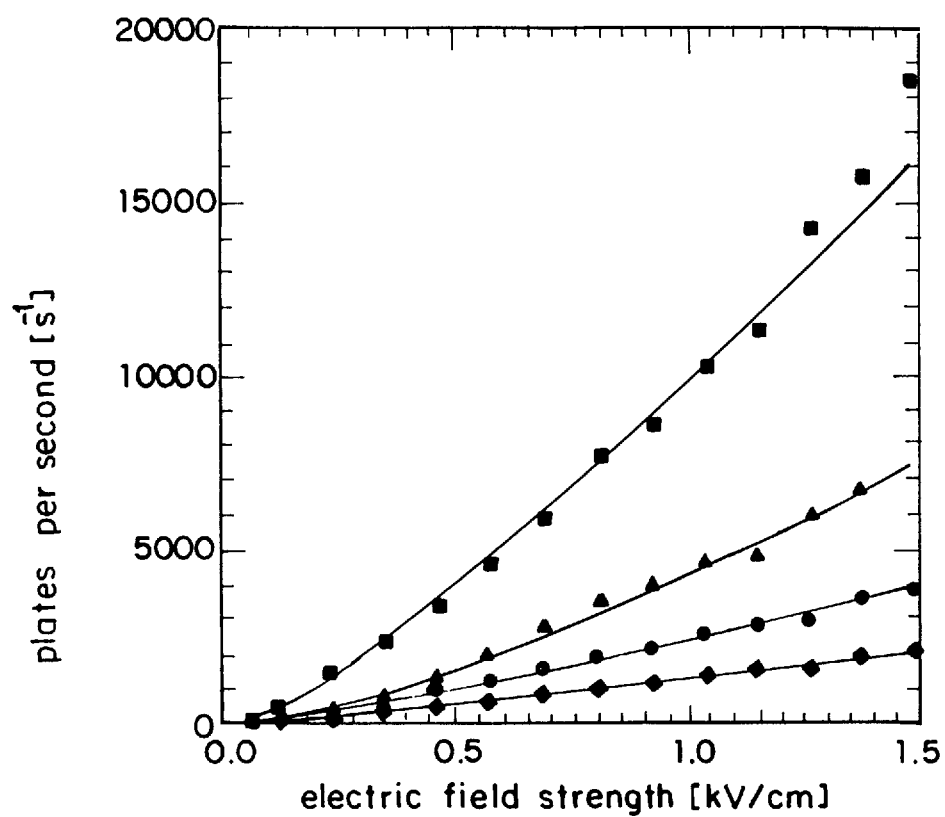
FIG. 18 is a graph showing variation of the number of plates per unit time as a function of the electric field strength for rhodamine B at separation lengths of 1.6 mm (circle) and 11.1 mm (square) and for fluorescein at separation lengths of 1.6 mm (diamond) and 11.1 mm (triangle)

In FIG. 18, the number of plates per second for the 1.6 mm and 11.1 mm separation lengths are plotted versus the electric field strength. The number of plates per second quickly becomes a linear function of the electric field strength, because the plate height approaches a constant value. The symbols in FIG. 18 represent the experimental data collected for the two analytes at the 1.6 mm and 11.1 mm separation lengths. The lines are calculated using the previously-stated equation and the coefficients are experimentally determined. A slight deviation is seen between the experimental data and the calculated numbers for rhodamine B at the 11.1 mm separation length. This is primarily due to experimental error.

Electrochromatography

A problem with electrophoresis for general analysis is its inability to separate uncharged species. All neutral species in a particular sample will have zero electrophoretic mobility, and thus, the same migration time. The microchip analyte injector 10D shown in FIG. 12 can also be used to perform electrochromatography to separate non-ionic analytes. To perform such electrochromatography, the surface of the separation channel 34D was prepared by chemically bonding a reverse, phase coating to the walls of the separation channel after bonding the cover plate to the substrate to enclose the channels. The separation channel was treated with 1M sodium hydroxide and then rinsed with water. The separation channel was dried at 125° C. for 24 hours while purging with helium at a gauge pressure of approximately 50 kPa. A 25% (w/w) solution of chlorodimethyloctaldecylsilane (ODS, Aldrich) in toluene was loaded into the separation channel with an over pressure of helium at approximately 90 kPa. The ODS/toluene mixture was pumped continuously into the column throughout the 18 hour reaction period at 125° C. The channels are rinsed with toluene and then with acetonitrile to remove the unreacted ODS. The laboratory system 10D was used to perform electrochromatography on an analytes composed of coumarin 440 (C440), coumarin 450 (C450) and coumarin 460 (C460, Exciton Chemical Co., Inc.) at 10 $\mu$M for the direct fluorescent measurements of the separations and 1 $\mu$M for the indirect fluorescent measurements of the void time. A sodium tetraborate buffer (10 mM, pH 9.2) with 25% (v/v) acetonitrile was the buffer.

The analyte injector 10D was operated under a pinched analyte loading mode and a separation (run) mode as described above with respect to FIG. 6. The analyte is loaded into the injection cross via a frontal chromatogram traveling from the analyte reservoir 16D to the analyte waste reservoir 18D, and once the front of the slowest analyte passes through the injection intersection 40D, the sample is ready to be analyzed. To switch to the separation mode, the applied potentials are reconfigured, for instance by manually throwing a switch. After switching the applied potentials, the primary flow path for the separation is from the buffer reservoir 12D to the waste reservoir 20D. In order to inject a small analyte plug into the separation channel 34D and to prevent bleeding of the excess analyte into the separation channel, the analyte and the analyte waste reservoirs 16D, 18D are maintained at 57% of the potential applied to the buffer reservoir 12D. This method of loading and injecting the sample is time-independent, non-biased and reproducible.

Figure 19:
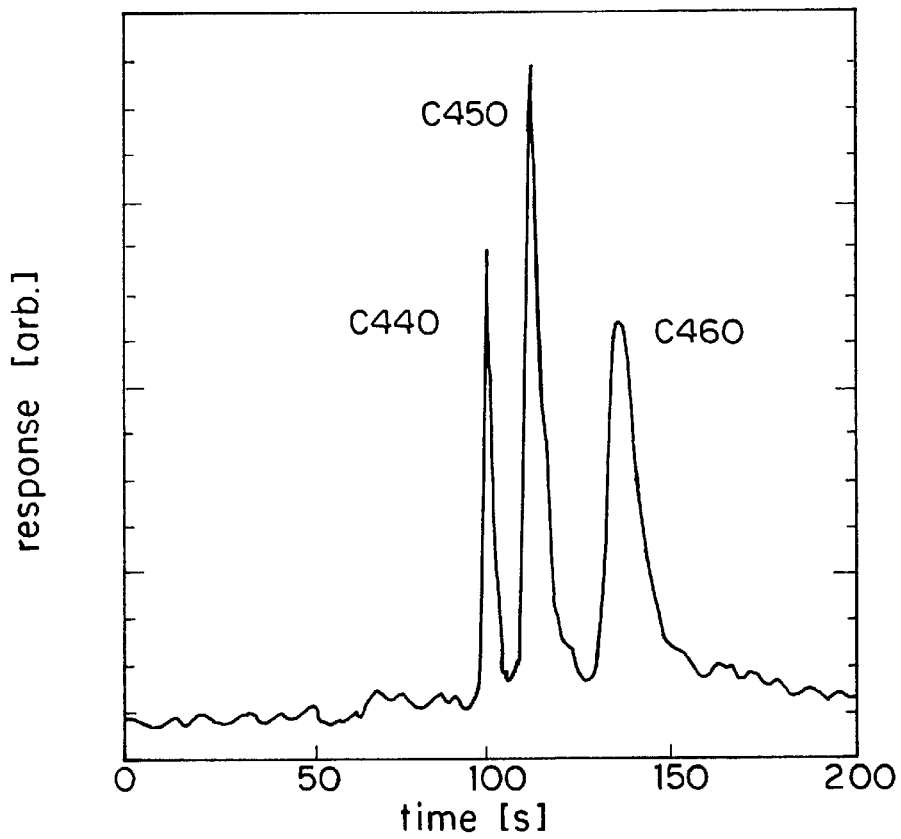
FIG. 19 shows a chromatogram of coumarins analyzed by electrochromatography using the system of FIG. 12.

In FIG. 19, a chromatogram of the coumarins is shown for a linear velocity of 0.65 mm/s. For C440, 11700 plates was observed which corresponds to 120 plates/s. The most retained component, C460, has an efficiency nearly an order of magnitude lower than for C440, which was 1290 plates. The undulating background in the chromatograms is due to background fluorescence from the glass substrate and shows the power instability of the laser. This, however, did not hamper the quality of the separations or detection. These results compare quite well with conventional laboratory High Performance LC (HPLC) techniques in terms of plate numbers and exceed HPLC in speed by a factor of ten. Efficiency is decreasing with retention faster than would be predicted by theory. This effect may be due to overloading of the monolayer stationary or kinetic effects due to the high speed of the separation.

Micellar Electrokinetic Capillary Chromatography

In the electrochromatography experiments discussed above with respect to FIG. 19, sample components were separated by their partitioning interaction with a stationary phase coated on the channel walls. Another method of separating neutral analytes is micellar electrokinetic capillary chromatography (MECC). MECC is an operational mode of electrophoresis in which a surfactant such as sodium dodecylsulfate (SDS) is added to the buffer in sufficient concentration to form micelles in the buffer. In a typical experimental arrangement, the micelles move much more slowly toward the cathode than does the surrounding buffer solution. The partitioning of solutes between the micelles and the surrounding buffer solution provides a separation mechanism similar to that of liquid chromatography.

The microchip laboratory 10D of FIG. 12 was used to perform on an analyte composed of neutral dyes coumarin 440 (C440), coumarin 450 (C450), and coumarin 460 (C460, Exciton Chemical Co., Inc.). Individual stock solutions of each dye were prepared in methanol then diluted into the analysis buffer before use. The concentration of each dye was approximately 50 $\mu$M unless indicated otherwise. The MECC buffer was composed of 10 mM sodium borate (pH 9.1), 50 mM SDS, and 10% (v/v) methanol. The methanol aids in solubilizing the coumarin dyes in the aqueous buffer system and also affects the partitioning of some of the dyes into the micelles. Due care must be used in working with coumarin dyes as the chemical, physical, and toxicological properties of these dyes have not been fully investigated.

The microchip laboratory system 10D was operated in the "pinched injection" mode described previously. The voltages applied to the reservoirs are set to either loading mode or a "run" (separation) mode. In the loading mode, a frontal chromatogram of the solution in the analyte reservoir 16D is pumped electroosmotically through the intersection and into the analyte waste reservoir 18D. Voltages applied to the buffer and waste reservoirs also cause weak flows into the intersection from the sides, and then into the analyte waste reservoir 18D. The chip remains in this mode until the slowest moving component of the analyte has passed through the intersection 40D. At this point, the analyte plug in the intersection is representative of the analyte solution, with no electrokinetic bias.

An injection is made by switching the chip to the "run" mode which changes the voltages applied to the reservoirs such that buffer now flows from the buffer reservoir 12D through the intersection 40D into the separation channel 34D toward the waste reservoir 20D. The plug of analyte that was in the intersection 40D is swept into the separation channel 34D. Proportionately lower voltages are applied to the analyte and analyte waste reservoirs 16D, 18D to cause a weak flow of buffer from the buffer reservoir 12D into these channels. These flows ensure that the sample plug is cleanly "broken off" from the analyte stream, and that no excess analyte leaks into the separation channel during the analysis.

Figure 20:
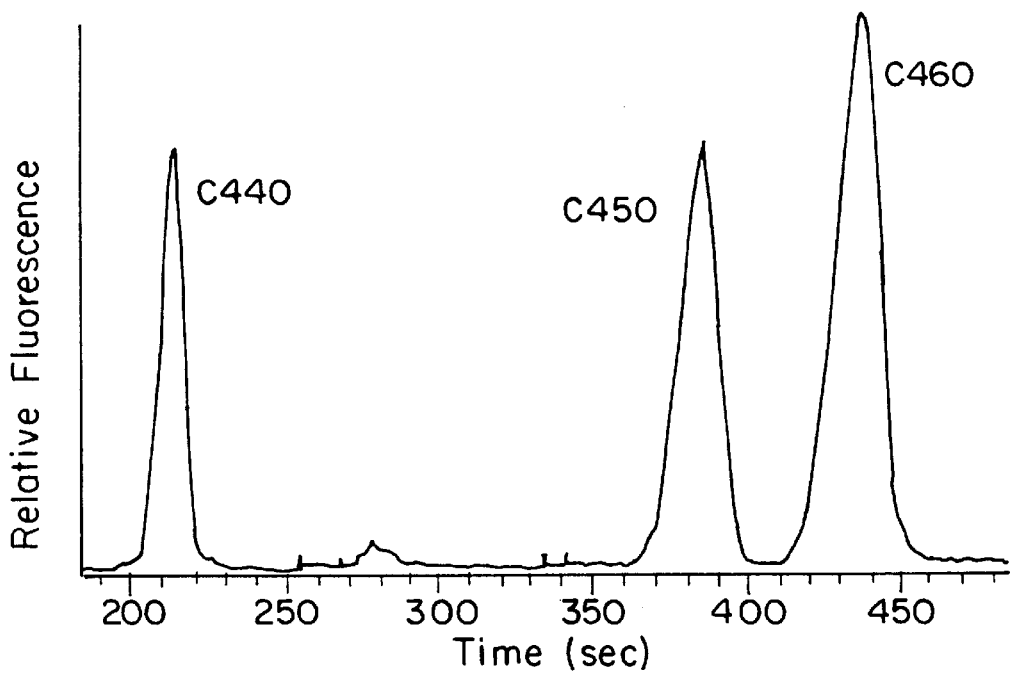
FIG. 20 shows a chromatogram of coumarins resulting from micellar electrokinetic capillary chromatography using the system of FIG. 12.

The results of the MECC analysis of a mixture of C440, C450, and C460 are shown in FIG. 20. The peaks were identified by individual analyses of each dye. The migration time stability of the first peak, C440, with changing methanol concentration was a strong indicator that this dye did not partition into the micelles to a significant extent. Therefore it was considered an electroosmotic flow marker with migration time t0. The last peak, C460, was assumed to be a marker for the micellar migration time, tm. Using these values of t0 and tm from the data in FIG. 20, the calculated elution range, t0/tm, is 0.43. This agrees well with a literature value of t0/tm =0.4 for a similar buffer system, and supports our assumption. These results compare well with conventional MECC performed in capillaries and also shows some advantages over the electrochromatography experiment described above in that efficiency is retained with retention ratio. Further advantages of this approach to separating neutral species is that no surface modification of the walls is necessary and that the stationary phase is continuously refreshed during experiments.

Inorganic Ion Analysis

Another laboratory analysis that can be performed on either the laboratory system 10B of FIG. 6 or the laboratory system 10D of FIG. 12 is inorganic ion analysis. Using the laboratory system 10B of FIG. 6, inorganic ion analysis was performed on metal ions completed with 8-hydroxyquinoline-5-sulfonic acid (HQS) which are separated by electrophoresis and detected with UV laser induced fluorescence. HQS has been widely used as a ligand for optical determinations of metal ions. The optical properties and the solubility of HQS in aqueous media have recently been used for detection of metal ions separated by ion chromatography and capillary electrophoresis. Because uncomplexed HQS does not fluoresce, excess ligand is added to the buffer to maintain the complexation equilibria during the separation without contributing a large background signal. This benefits both the efficiency of the separation and detectability of the sample. The compounds used for the experiments are zinc sulfate, cadmium nitrate, and aluminum nitrate. The buffer is sodium phosphate (60 mM, pH 6.9) with 8-hydroxyquinoline-5-sulfonic acid (20 mM for all experiments except FIG. 5; Sigma Chemical Co.). At least 50 mM sodium phosphate buffer is needed to dissolve up to 20 mM HQS. The substrate 49B used was fused quartz which provides greater visibility than glass substrates.

The floating or pinched analyte loading, as described previously with respect to FIG. 6, is used to transport the analyte to the injection intersection 40B. With the floating sample loading, the injected plug has no electrophoretic bias, but the volume of sample is a function of the sample loading time. Because the sample loading time is inversely proportional to the field strength used, for high injection field strengths a shorter injection time is used than for low injection field strengths. For example, for an injection field strength of 630 V/cm (FIG. 3a), the injection time is 12 s, and for an injection field strength of 520 V/cm FIG. 3b), the injection time is 14.5 s. Both the pinched and floating sample loading can be used with and without suppression of the electroosmotic flow.

Figure 21A:
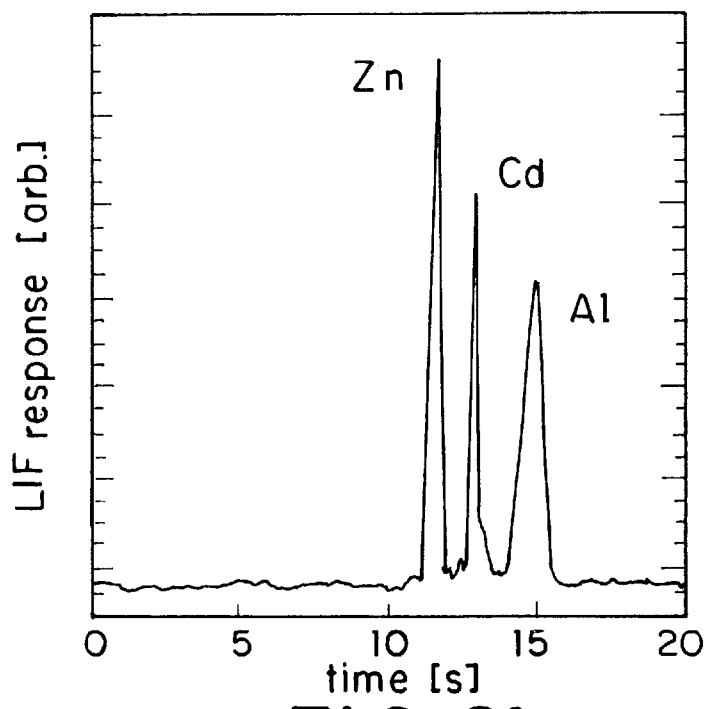
FIGS. 21(a) and 21(b) show the separation of three metal ions using the system of FIG. 12.
Figure 21B:
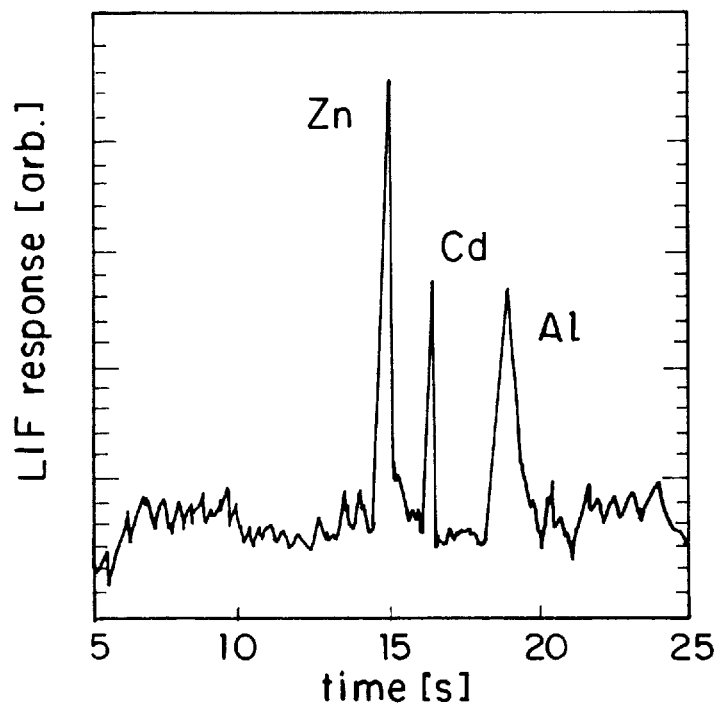

FIGS. 21(a) and 21(b) show the separation of three metal ions complexed with 8-hydroxyquinoline-5-sulfonic acid. All three complexes have a net negative charge. With the electroosmotic flow minimized by the covalent bonding of polyacrylamide to the channel walls, negative potentials relative to ground are used to manipulate the complexes during sample loading and separation. In FIGS. 21(a) and 21(b), the separation channel field strength is 870 and 720 V/cm, respectively, and the separation length is 16.5 mm. The volume of the injection plug is 120 pL which corresponds to 16, 7, and 19 fmol injected for Zn, Cd, and Al, respectively, for FIG. 4a. In FIG. 4b, 0.48, 0.23, and 0.59 fmol of Zn, Cd, and Al, respectively, are injected onto the separation column. The average reproducibility of the amounts injected is 1.6% rsd (percent relative standard deviation) as measured by peak areas (6 replicate analyses). The stability of the laser used to excite the complexes is ≈1% rsd. The detection limits are in a range where useful analyses can be performed.

Post-Separation Channel Reactor

Figure 22:
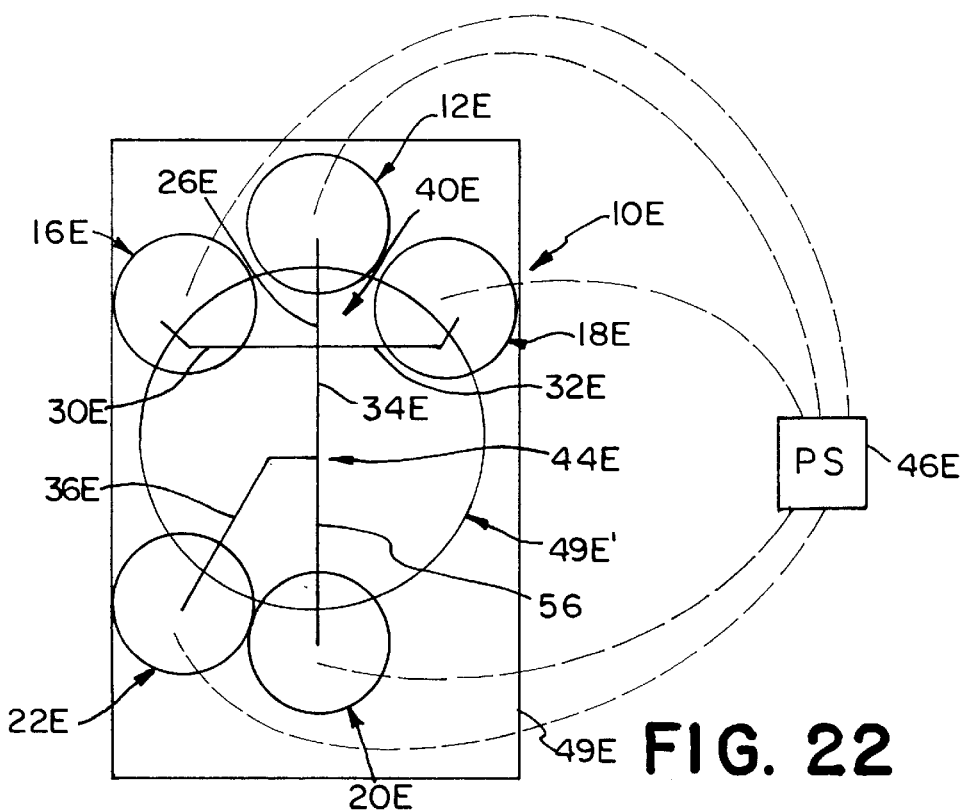
FIG. 22 is a schematic, top plan view of a microchip according to the FIG. 3 embodiment, additionally including a reagent reservoir and reaction channel.

An Iternate microchip laboratory system 10E is shown in FIG. 22. The five-port pattern of channels is disposed on a substrate 49E and with a cover slip 49E', as in the previously-described embodiments. The microchip laboratory system 10E embodiment was fabricated using standard photolithographic, wet chemical etching, and bonding techniques. A photomask was fabricated by sputtering chrome (50 nm) onto a glass slide and ablating the channel design into the chrome film via a CAD/CAM laser ablation system Resonetics, Inc.). The channel design was then transferred onto the substrates using a positive photoresist. The channels were etched into the substrate in a dilute $Hf/Nh_4F$ bath. To form the separation channel 34E, a coverplate was bonded to the substrate over the etched channels using a direct bonding technique. The surfaces were hydrolyzed in dilute $NH_4OH/H_2O_2$ solution, rinsed in deionized, filtered $H_2$, joined and then annealed at 500° C. Cylindrical glass reservoirs were affixed on the substrate using RTV silicone (made by General Electric). Platinum electrodes provided electrical contact from the voltage controller 46E (Spellman CZE1000R) to the solutions in the reservoirs.

The channel 26E is in one embodiment 2.7 mm in length from the first reservoir 12E to the intersection 40E, while the channel 30E is 1.0 mm, and the third channel 32E is 6.7 mm. The separation channel 34E is modified to be only 7.0 mm in length, due to the addition of a reagent reservoir 22E which has a reagent channel 36E that connects to the separation channel 34E at a mixing tee 44E. Thus, the length of the separation channel 34E is measured from the intersection 40E to the mixing tee 44E. The channel 56 extending from the mixing tee 44E to the waste reservoir 20E is the reaction column or channel, and in the illustrated embodiment this channel is 10.8 mm in length. The length of the reagent channel 36E is 11.6 mm.

In a representative example, the FIG. 22 embodiment was used to separate an analyte and the separation was monitored on-microchip via fluorescence using an argon ion laser (351.1 nm, 50 mW, Coherent Innova 90) for excitation. The fluorescence signal was collected with a photomultiplier tube (PMT, Oriel 77340) for point detection and a charge coupled device (CCD. Princeton Instruments, Inc. TE/CCD-512TKM) for imaging a region of the microchip 90. The compounds used for testing the apparatus were rhodamine B (Exciton Chemical Co., Inc.) arginine, glycine, threonine and o-phthaldialdehyde (Sigma Chemical Co.) A sodium tetraborate buffer (20 mM pH 9.2) with 2% (v/v) methanol and 0.5% (v/v) β-mercaptoethanol was the buffer in all tests. The concentrations of the amino acid, OPA and rhodamine B solutions were 2 mM, 3.7 mM, and 50 $\mu$M, respectively. Several run conditions were utilized.

Figure 23:
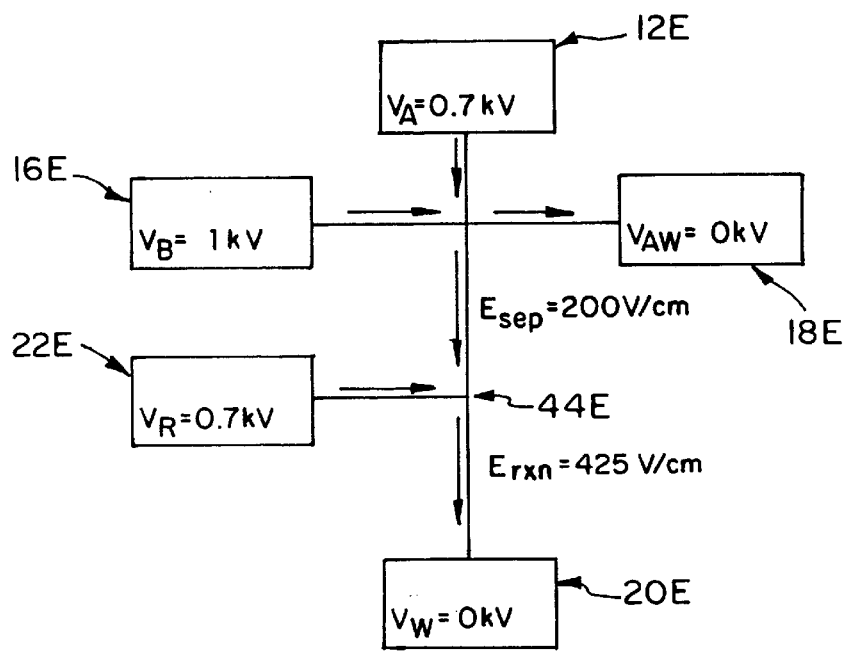
FIG. 23 is a schematic view of the embodiment of FIG. 20, showing applied voltages.

The schematic view in FIG. 23 demonstrates one example when 1 kV is applied to the entire system. With this voltage configuration, the electric field strengths in the separation channel 34E ($E_{scp}$) and the reaction channel 36E ($E_{ixm}$) are 200 and 425 V/cm, respectively. This allows the combining of 1 part separation effluent with 1.125 parts reagent at the mixing tee 44E. An analyte introduction system such as this, with or without post-column reaction, allows a very rapid cycle time for multiple analyses.

Figure 24A:
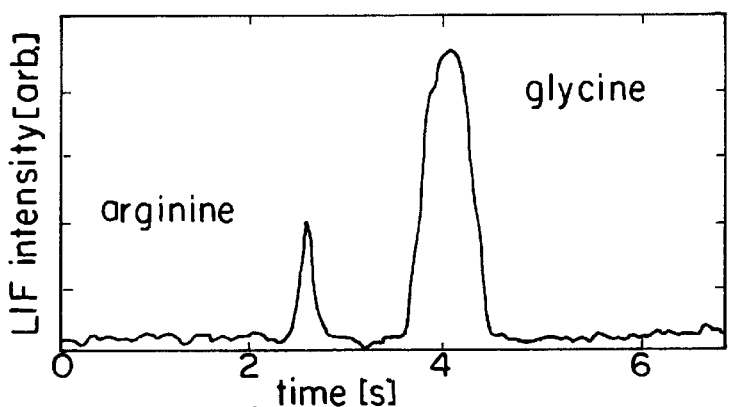
FIG. 24 shows two electropherograms produced using the FIG. 22 embodiment.
Figure 24B:
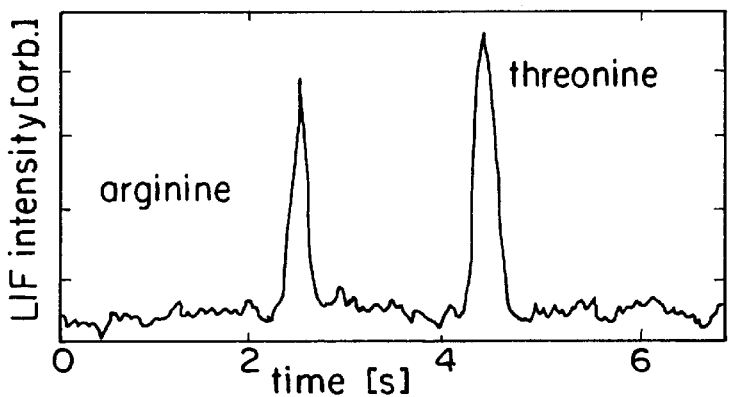

The electropherograms; (A) and (B) in FIG. 24 demonstrate the separation of two pairs of amino acids. The voltage configuration is the same as in FIG. 23, except the total applied voltage is 4 kV which corresponds to an electric field strength of 800 V/cm in the separation column ($E_{scp}$) and 1,700 V/cm in the reaction column ($E_r$). The injection times were 100 ms for the tests which correspond to estimated injection plug lengths of 384, 245, and 225 $\mu$m for arginine, glycine and threonine, respectively. The injection volumes of 102, 65, and 60 pL correspond to 200, 130, and 120 fmol injected for arginine, glycine and threonine, respectively. The point of detection is 6.5 mm downstream from the mixing tee which gives a total column length of 13.5 mm for the separation and reaction.

The reaction rates of the amino acids with the OPA are moderately fast, but not fast enough on the time scale of these experiments. An increase in the band distortion is observed because the mobilities of the derivatized compounds are different from the pure amino acids. Until the reaction is complete, the zones of unreacted and reacted amino acid will move at different velocities causing a broadening of the analyte zone. As evidenced in FIG. 24, glycine has the greatest discrepancy in electrophoretic mobilities between the derivatized and un-derivatized amino acid. To ensure that the excessive band broadening was not a function of the retention time, threonine was also tested. Threonine has a slightly longer retention time than the glycine; however the broadening is not as extensive as for glycine.

To test the efficiency of the microchip in both the separation column and the reaction column, a fluorescent laser dye, rhodamine B, was used as a probe. Efficiency measurements calculated from peak widths at half height were made using the point detection scheme at distances of 6 mm and 8 mm from the injection cross, or 1 mm upstream and 1 mm downstream from the mixing tee. This provided information on the effects of the mixing of the two streams.

The electric field strengths in the reagent column and the separation column were approximately equal, and the field strength in the reaction column was twice that of the separation column. This configuration of the applied voltages allowed an approximately 1:1 volume ratio of derivatizing reagent and effluent from the separation column. As the field strengths increased, the degree of turbulence at the mixing tee increased. At the separation distance of 6 mm (1 mm upstream from the mixing tee), the plate height as expected as the inverse of the linear velocity of the analyte. At the separation distance of 8 mm (1 mm upstream from the mixing tee), the plate height data decreased as expected as the inverse of the velocity of the analyze. At the separation distance of 8 mm (1 mm downstream from the mixing tee), the plate height data decreases from 140 V/cm to 280 V/cm to 1400 V/cm. This behavior is abnormal and demonstrates a band broadening phenomena when two streams of equal volumes converge. The geometry of the mixing tee was not optimized to minimize this band distortion. Above separation field strength of 840 V/cm, the system stabilizes and again the plate height decreases with increasing linear velocity For $E_{scp}$=1400 V/cm, the ratio of the plate heights at the 8 mm and 6 mm separation lengths is 1.22 which is not an unacceptable loss in efficiency for the separation.

The intensity of the fluorescence signal generated from the reaction of OPA with an amino acid was tested by continuously pumping glycine down the separation channel to mix with the OPA at the mixing tee. The fluorescence signal from the OPA/amino acid reaction was collected using a CCD as the product moved downstream from the mixing tee. Again, the relative volume ratio of the OPA and glycine streams was 1.125. OPA has a typical half-time of reaction with amino acids of 4 s. The average residence times of an analyte molecule in the window of observation are 4.68, 2.34, 1.17, and 0.58 s for the electric field strengths in the reaction column ($E_{irm}$) of 240, 480, 960, and 1920 V/cm respectively. The relative intensities of the fluorescence correspond qualitatively to this 4 s half-time of reaction. As the field strength increases in the reaction channel, the slope and maximum of the intensity of the fluorescence shifts further downstream because the glycine and OPA are swept away from the mixing tee faster with higher field strengths. Ideally, the observed fluorescence from the product would have a step function of a response following the mixing of the separation effluent and derivatizing reagent. However, the kinetics of the reaction and a finite rate of mixing dominated by diffusion prevent this from occurring.

The separation using the post-separation channel reactor employed a gated injection scheme in order to keep the analyte, buffer and reagent streams isolated as discussed above with respect to FIG. 3. For the post-separation channel reactions, the microchip was operated in a continuous analyte loading/separation mode whereby the analyte was continuously pumped from the analyte reservoir 12E through the injection intersection 40E toward the analyte waste reservoir 18E. Buffer was simultaneously pumped from the buffer reservoir 16E toward the analyte waste and waste reservoirs 18E, 20E to deflect the analyte stream and prevent the analyte from migrating down the separation channel. To inject a small aliquot of analyte, the potentials at the buffer and analyte waste reservoirs 16F, 18E are simply floated for a short period of time (≈100 ms) to allow the analyte to migrate down the separation channel as an analyte injection plug. To break off the injection plug, the potentials at the buffer and analyte waste reservoirs 16E, 18E are reapplied.

The use of micromachined post-column reactors can improve the power of post-separation channel reactions as an analytical tool by minimizing the volume of the extra-channel plumbing, especially between the separation and reagent channels 34E, 36E. This microchip design (FIG. 22) was fabricated with modest lengths for the separation channel 34E (7 mm) and reagent channel 36E (10.8 mm) which were more than sufficient for this demonstration. Longer separation channels can be manufactured on a similar size microchip using a serpentine path to perform more difficult separations as discussed above with respect to FIG. 12. To decrease post-mixing tee band distortions, the ratio of the channel dimensions between the separation channel 34E and reaction channel 56 should be minimized so that the electric field strength in the separation channel 34E is large, i.e., narrow channel, and in the reaction channel 56 is small, i.e., wide channel.

For capillary separation systems, the small detection volumes can limit the number of detection schemes that can be used to extract information. Fluorescence detection remains one of the most sensitive detection techniques for capillary electrophoresis. When incorporating fluorescence detection into a system that does not have naturally fluorescing analytes, derivatization of the analyte must occur either pre- or post-separation. When the fluorescent "tag" is short lived or the separation is hindered by pre-separation derivatization, post-column addition of derivatizing reagent becomes the method of choice. A variety of post-separation reactors have been demonstrated for capillary electrophoresis. However, the ability to construct a post-separation reactor with extremely low volume connections to minimize band distortion has been difficult. The present invention takes the approach of fabricating a microchip device for electrophoretic separations with an integrated post-separation reaction channel 56 in a single monolithic device enabling extremely low volume exchanges between individual channel functions.

Pre-Separation Channel Reaction System

Figure 25:
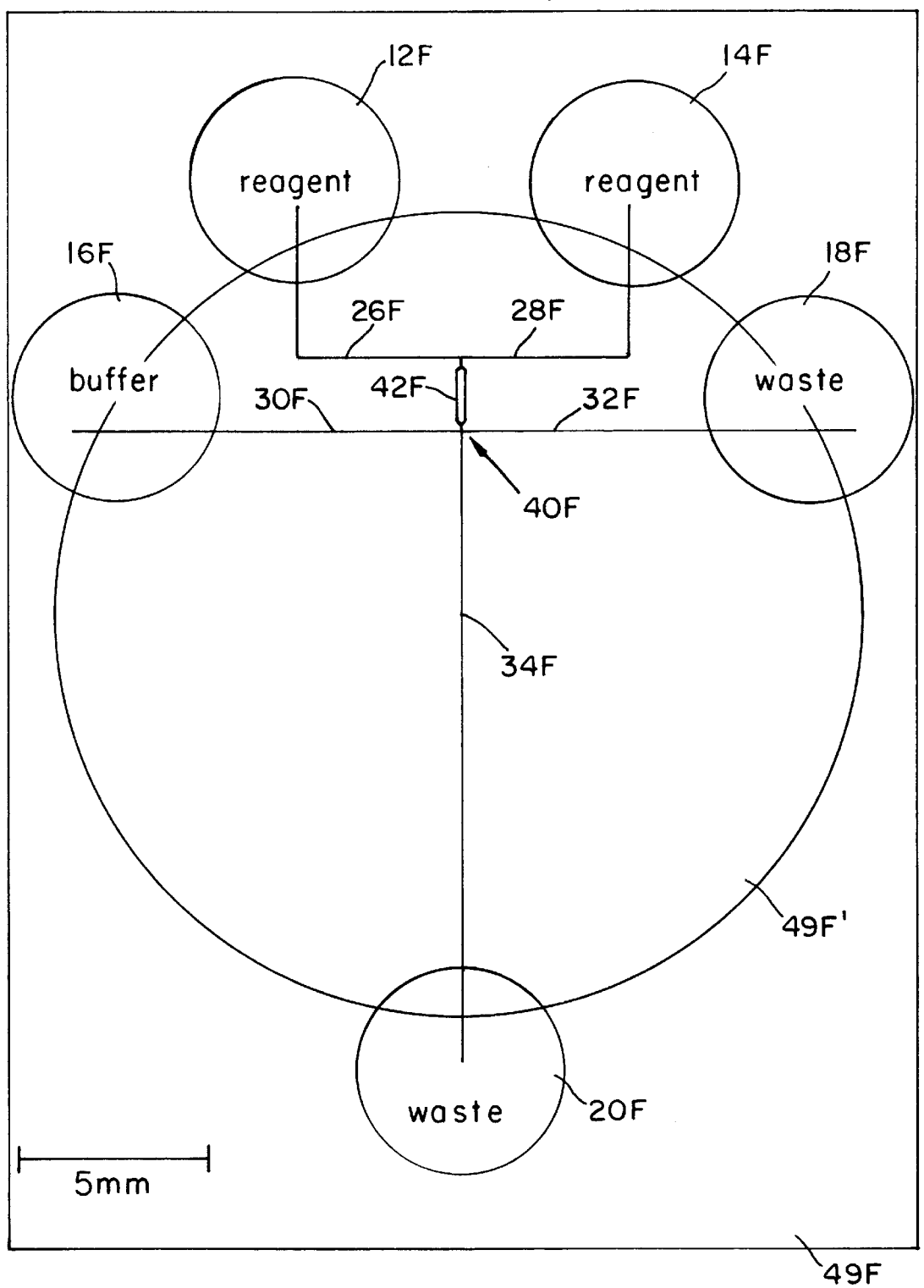
FIG. 25 is a schematic view of a microchip laboratory system according to a sixth preferred embodiment of the present invention.

Instead of the post-separation channel reactor design shown in FIG. 22, the microchip laboratory system 10F shown in FIG. 25 includes a pre-separation channel reactor. The pre-separation channel reactor design shown in FIG. 25 is similar to that shown in FIG. 1, except that the first and second channels 26F, 28F form a "goal-post" design with the reaction chamber 42F rather than the "Y" design of FIG. 1. The reaction chamber 42F was designed to be wider than the separation channel 34F to give lower electric field strengths in the reaction chamber and thus longer residence times for the reagents. The reaction chamber is 96 $\mu$m wide at half-depth and 6.2 $\mu$m deep, and the separation channel 34F is 31 $\mu$m wide at half-depth and 6.2 $\mu$m deep.

The microchip laboratory system 10F was used to perform on-line pre-separation channel reactions coupled with electrophoretic analysis of the reaction products. Here, the reactor is operated continuously with small aliquots introduced periodically into the separation channel 34F using the gated dispenser discussed above with respect to FIG. 3. The operation of the microchip consists of three elements: the derivatization of amino acids with o-phthaldialdehyde (OPA), injection of the sample onto the separation column, and the separation/ detection of the components of the reactor effluent. The compounds used for the experiments were arginine (0.48 mM, glycine (0.58mM), and OPA (5.1 mM; Sigma Chemical Co). The buffer in all of the reservoirs was 20 mM sodium tetraborate with 2% (v/v) methanol and 0.5% (v/v) 2-mercaptoethanol. 2-mercaptoethanol is added to the buffer as a reducing agent for the derivatization reaction.

To implement the reaction the reservoirs 12F, 14F, 16F, 18F, and 20F were simultaneously given controlled voltages of 0.5 HV, 0.5 HV, HV. 0.2 HV, and ground, respectively. This configuration allowed the lowest potential drop across the reaction chamber 42F (25 V/cm for 1.0 kV applied to the microchip) and highest across the separation channel 34F (300 V/cm for 1.0 kV applied to the microchip) without significant bleeding of the product into the separation channel when using the gated injection scheme. The voltage divider used to establish the potentia's applied to each of the reservoirs had a total resistance of 100M$\Omega$ with 10M$\Omega$ divisions. The analyte from the first reservoir 12F and the reagent from the second reservoir 14F are electroosmotically pumped into the reaction chamber 42F with a volumetric ratio of 1:1.06. Therefore, the solutions from the analyte and reagent reservoirs 12F, 14F are diluted by a factor of ≈2. Buffer was simultaneously pumped by electroosmosis from the buffer reservoir 16 toward the analyte waste and waste reservoirs 18F, 20F. This buffer stream prevents the newly formed product from bleeding into the separation channel 34F.

Preferably, a gated injection scheme, described above with respect to FIG. 3, is used to inject effluent from the reaction chamber 42F into the separation channel 34F. The potential at the buffer reservoir 16F is simply floated for a brief period of time (0.1 to 1.0 s), and sample migrates into the separation channel 34F. To break off the injection plug, the potential at the buffer reservoir 16F is reapplied. The length of the injection plug is a function of both the time of the injection and the electric field strength. With this configuration of applied potentials, the reaction of the amino acids with the OPA continuously generates fresh product to be analyzed.

Figure 26:
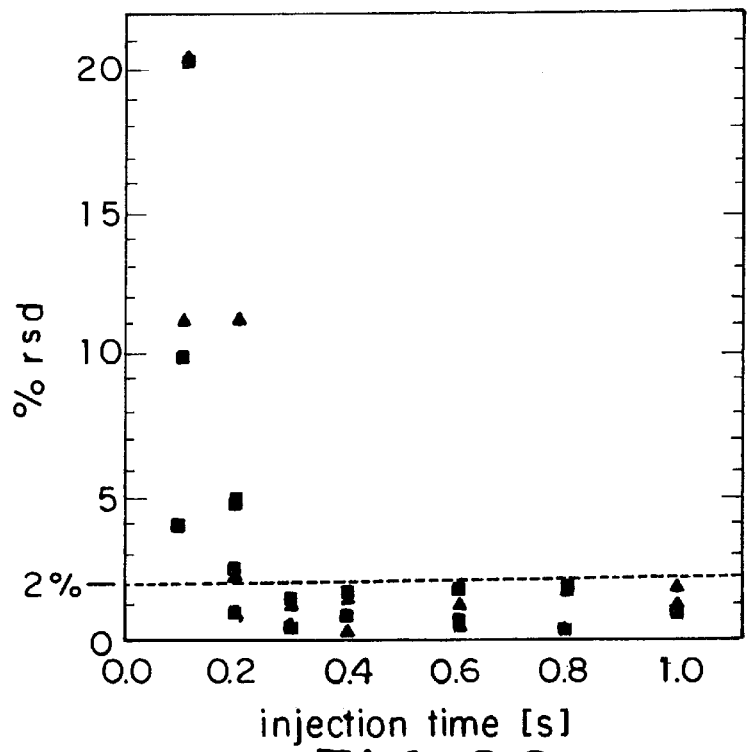
FIG. 26 shows the reproducibility of the amount injected for arginine and glycine using the system of FIG. 25.

A significant shortcoming of many capillary electrophoresis experiments has been the poor reproducibility of the injections. Here, because the microchip injection process is computer controlled, and the injection process involves the opening of a single high voltage switch, the injections can be accurately timed events. FIG. 26 shows the reproducibility of the amount injected (percent relative standard deviation, % rsd, for the integrated areas of the peaks) for both arginine and glycine at injection field strengths of 0.6 and 1.2 kV/cm and injection times ranging from 0.1 to 1.0 s. For injection times greater than 0.3 s, the percent relative standard deviation is below 1.8%. This is comparable to reported values for commercial, automated capillary electrophoresis instruments. However, injections made on the microchip are ≈100 times smaller in volume, e.g. 100 pL on the microchip versus 10 nL on a commercial instrument. Part of this fluctuation is due to the stability of the laser which is ≈0.6%. For injection times>0.3 s, the error appears to be independent of the compound injected and the injection field strength.

Figure 27:
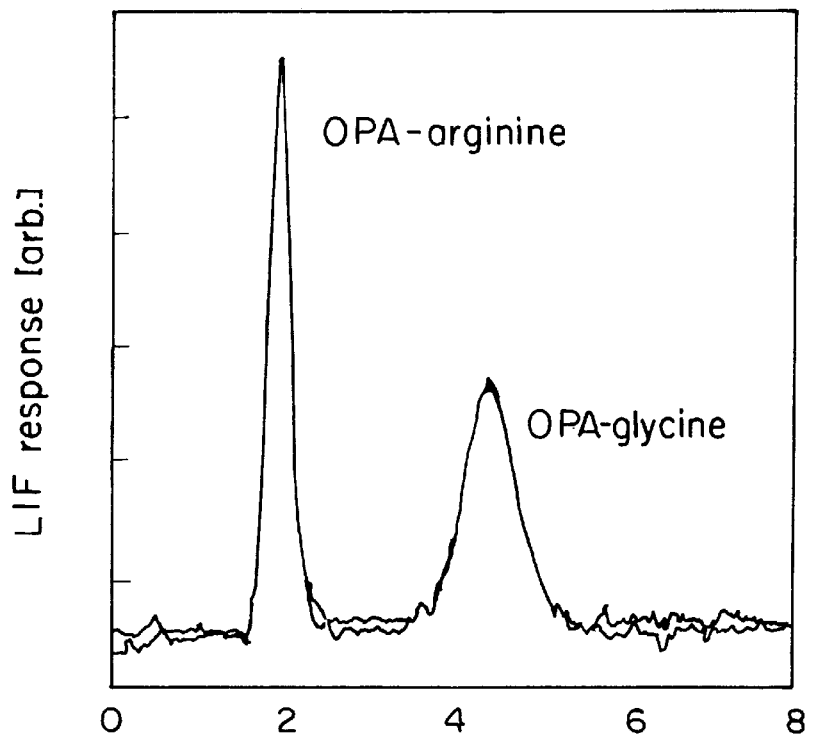
FIG. 27 shows the overlay of three electrophoretic separations using the system of FIG. 25.

FIG. 27 shows the overlay of three electrophoretic separations of arginine and glycine after on-microchip pre-column derivatization with OPA with a separation field strength of 1.8 kV/cm and a separation length of 10 mm. The separation field strength is the electric field strength in the separation channel 34F during the separation. The field strength in the reaction chamber 42F is 150 V/cm. The reaction times for the analytes is inversely related to their mobilities. e.g., for arginine the reaction time is 4.1 s and for glycine the reaction time is 89 s. The volumes of the injected plugs were 150 and 71 pL for arginine and glycine, respectively, which correspond to 35 and 20 fmol of the amino acids injected onto the separation channel 34F. The gated injector allows rapid sequential injections to be made. In this particular case, in analysis could be performed every 4 s. The observed electrophoretic mobilities for the compounds are determined by a linear fit to the variation of the linear velocity with the separation field strength. The slopes were 29.1 and 13.3 $mm^2/(kV \cdot s)$ for arginine and glycine, respectively. No evidence of Joule heating was observed as indicated by the linearity of the velocity versus field strength data. A linear fit produced correlation coefficients of 0.999 for arginine and 0.996 for glycine for separation field strength from 0.2 to 2.0 kV/cm.

Figure 28:
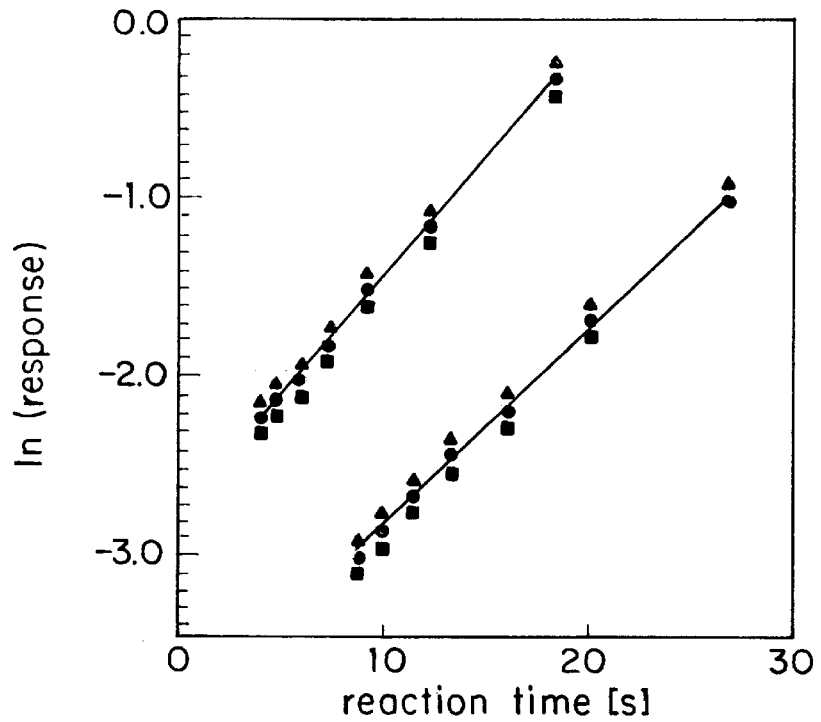
FIG. 28 shows a plot of amounts injected versus reaction time using the system of FIG. 25.

With increasing potentials applied to the microchip Laboratory system 10F, the field strengths in the reaction chamber 42F and separation channel 34F increase. This leads to shorter residence times of the reactants in the reaction chamber and faster analysis times for the products. By varying the potentials applied to the microchip, the reaction kinetics can be studied. The variation in amount of product generated with reaction time is plotted in FIG. 28. The response is the integrated area of the peak corrected for the residence time in the detector observation window and photobleaching of the product. The offset between the data for the arginine and the glycine in FIG. 28 is due primarily to the difference in the amounts injected, i.e. different electrophoretic mobilities, for the amino acids. A ten-fold excess of OPA was used to obtain pseudo-first order reaction conditions. The slopes of the lines fitted to the data correspond to the rates of the derivatization reaction. The slopes are $0.13 \, s^{-1}$ for arginine and $0.11 \, s^{-1}$ for glycine corresponding to half-times of reaction of 5.1 and 6.2 s, respectively. These half-times of reaction are comparable to the 4 s previously reported for alanine. We have found no previously reported data for arginine or glycine.

These results show the potential power of integrated microfabricated systems for performing chemical procedures. The data presented in FIG. 28 can be produced under computer control within five approximately five minutes consuming on the order of 100 nL of reagents. These results are unprecedented in terms of automation, speed and volume for chemical reactions.

DNA Analysis

Figure 29:
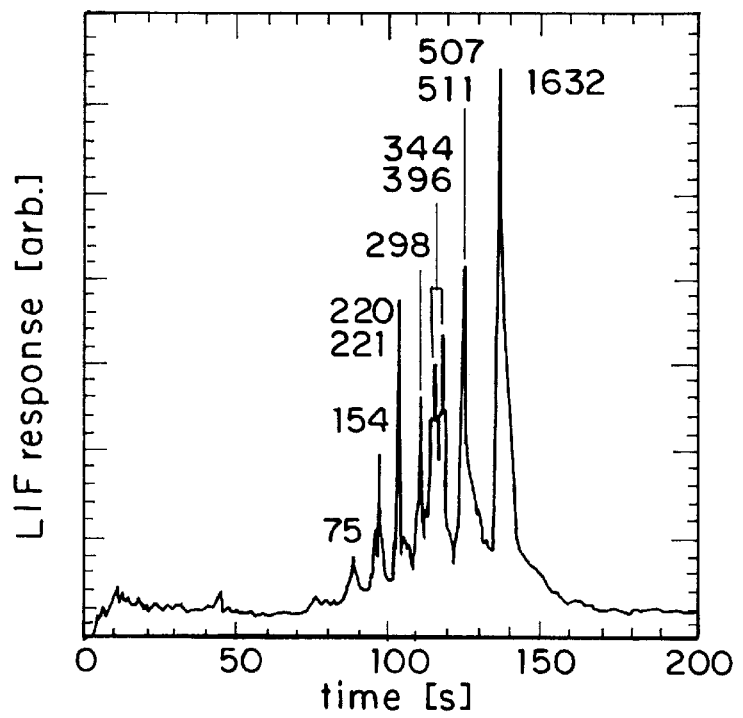
FIG. 29 shows an electropherogram of restriction fragments produced using the system of FIG. 25.

To demonstrate a useful biological analysis procedure, a restriction digestion and electrophoretic sizing experiment are performed sequentially on the integrated biochemical reactor/electrophoresis microchip system 10G shown in FIG. 29. The microchip laboratory system 10G is identical to the laboratory system shown in FIG. 25 except that the separation channel 34G of the laboratory system 10G follows a serpentine path. The sequence for plasmid pBR322 and the recognition sequence of the enzyme Hinf I are known. After digestion, determination of the fragment distribution is performed by separating the digestion products using electrophoresis in a sieving medium in the separation channel 34G. For these experiments, hydroxyethyl cellulose is used as the sieving medium. At a fixed point downstream in the separation channel 34G, migrating fragments are interrogated using on-chip laser induced fluorescence with an intercalating dye, thiazole orange dimer (TOTO-1), as the fluorophore.

The reaction chamber 42G and separation channel 34G shown in FIG. 29 are 1 and 67 mm long, respectively, having a width at half-depth of 60 $\mu$m and a depth of 12 $\mu$m. In addition, the channel walls are coated with polyacrylamide to minimize electroosmotic flow and adsorption. Electropherograms are generated using single point detection laser induced fluorescence detection. An argon ion laser (10 mW) is focused to a spot onto the chip using a lens (100 mm focal length). The fluorescence signal is collected using a 21×objective lens (N.A.=0.42), followed by spatial filtering (0.6 mm diameter pinhole) and spectral filtering (560 nm bandpass, 40 nm bandwidth), and measured using a photomultiplier tube (PMT). The data acquisition and voltage switching apparatus are computer controlled. The reaction buffer is 10 mM Tris-acetate, 10 mM magnesium acetate, and 50 mM potassium acetate. The reaction buffer is placed in the DNA, enzyme and waste I reservoirs 12G, 14G, 18G shown in FIG. 29. The separation buffer is 9 mM Tris-borate with 0.2 mM EDTA and 1% (w/v) hydroxyethyl cellulose. The separation buffer is placed in the buffer and waste 2 reservoirs 16F, 20F. The concentrations of the plasmid pBR322 and enzyme Hinf I are 125 ng/$\mu$l and 4 units/$\mu$l, respectively. The digestions and separations are performed at room temperature (20° C.).

The DNA and enzyme are electrophoretically loaded into the reaction chamber 42G from their respective reservoirs 120, 14G by application of proper electrical potentials. The relative potentials at the DNA (12G), enzyme (14G), buffer (16G), waste 1 (18G), and waste 2 (20G) reservoirs are 10%, 10% 0.30%, and 100%, respectively. Due to the electrophoretic mobility differences between the DNA and enzyme, the loading period is made sufficiently long to reach equilibrium. Also, due to the small volume of the reaction chamber 42G, 0.7 nL, rapid diffusional mixing occurs. The electroosmotic flow is minimized by the covalent immobilization of linear polyacrylamide, thus only anions migrate from the DNA and enzyme reservoirs 12G, 14G into the reaction chamber 42G with the potential distributions used. The reaction buffer which contains cations required for the enzymatic digestions, e.g. $Mg^{2+}$, is also placed in the waste 1 reservoir 18G. This enables the cations to propagate into the reaction chamber countercurrent to the DNA and enzyme during the loading of the reaction chamber. The digestion is performed statically by removing all electrical potentials after loading the reaction chamber 42G due to the relatively short transit time of the DNA through the reaction chamber.

Following the digestion period, the products are migrated into the separation channel 34F for analysis by floating the voltages to the buffer and waste 1 reservoirs 16F, 18F. The injection has a mobility bias where the smaller fragments are injected in favor of the larger fragments. In these experiments the injection plug length for the 75-base pair (bp) fragment is estimated to be 0.34 mm whereas for the 1632-bp fragment only 0.22 mm. These plug lengths correspond to 34% and 22% of the reaction chamber volume, respectively. The entire contents of the reaction chamber 42F cannot be analyzed under current separation conditions because the contribution of the injection plug length to the plate height would be overwhelming.

Figure 30:
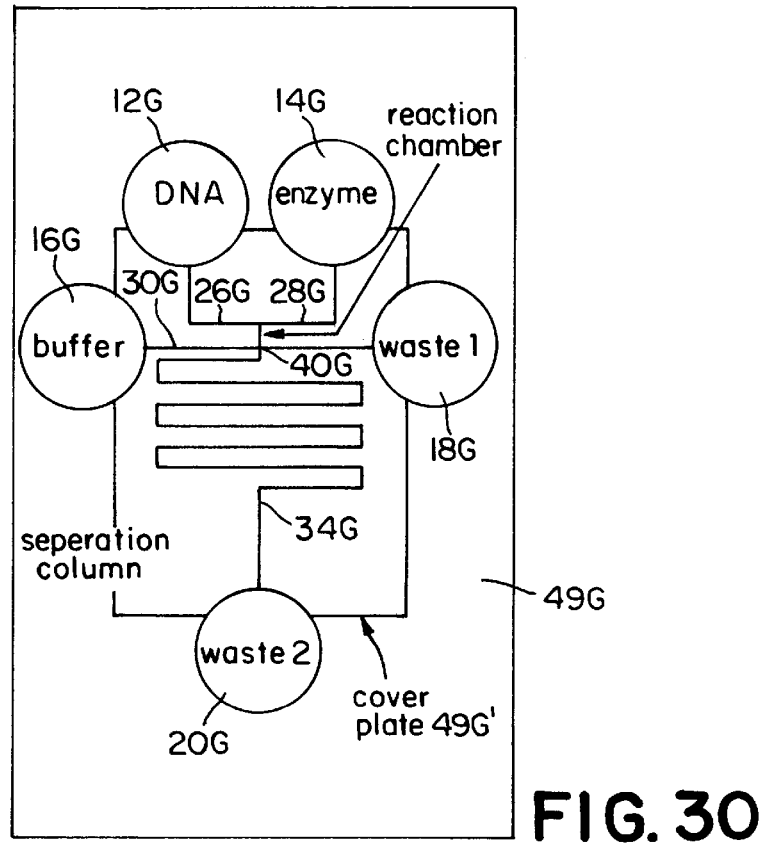
FIG. 30 is a schematic view of a microchip laboratory system according to a seventh preferred embodiment of the present invention.

Following digestion and injection onto the separation channel 34F, the fragments are resolved using 1.0% (w/v) hydroxyethyl cellulose as the sieving medium. FIG. 30 shows an electropherogram of the restriction fragments of the plasmid pBR322 following a 2 min digestion by the enzyme Hinf I. To enable efficient on-column staining of the double-stranded DNA after digestion but prior to interrogation, the intercalating dye, TOTO-1 (1 $\mu$M), is placed in the waste 2 reservoir 20G only and migrates countercurrent to the DNA. As expected, the relative intensity of the bands increases with increasing fragment size because more intercalation sites exist in the larger fragments. The unresolved 220/221 and 507/511-bp fragments having higher intensities than adjacent single fragment peaks due to the band overlap. The reproducibility of the migration times and injection volumes are 0.55 and 3.1% relative standard deviation (%/rsd), respectively, for 5 replicate analyses.

This demonstration of a microchip laboratory system 10G that performs plasmid DNA restriction fragment analysis indicates the possibility of automating and miniaturizing more sophisticated biochemical procedures. This experiment represents the most sophisticated integrated microchip chemical analysis device demonstrated to date. The device mixes a reagent with an analyte, incubates the analyte/reagent mixture, labels the products, and analyzes the products entirely under computer control while consuming 10,000 times less material than the typical small volume laboratory procedure.

In general, the present invention can be used to mix different fluids contained in different ports or reservoirs. This could be used for a liquid chromatography separation experiment followed by post-column labeling reactions in which different chemical solutions of a given volume are pumped into the primary separation channel and other reagents or solutions can be injected or pumped into the stream at different times to be mixed in precise and known concentrations. To execute this process, it is necessary to accurately control and manipulate solutions in the various channels.

Pre-/Post-Separation Reactor System

FIG. 31 shows the same six port microchip laboratory system 10 shown in FIG. 1, which could take advantage of this novel mixing scheme. Particular features attached to the different ports represent solvent reservoirs. This laboratory system could potentially be used for a liquid chromatography separation experiment followed by post-column labeling reactions. In such an experiment, reservoirs 12 and 14 would contain solvents to be used in a liquid chromatography solvent programming type of separation, e.g., water and acetonitrile.

The channel 34 connected to the waste reservoir 2) and to the two channels 26 and 28 connecting the analyte and solvent reservoirs 12 and 14 is the primary separation channel, i.e., where the liquid chromatography experiment would take place. The intersecting channels 30, 32 connecting the buffer and analyte waste reservoirs 16 and 18 are used to make an injection into the liquid chromatography or separation channel 34 as discussed above. Finally, reservoir 22 and its channel 36 attaching to the separation channel 34 are used to add a reagent, which is added in proportions to render the species separated in the separation channel detectable.

To execute this process, it is necessary to accurately control and manipulate solutions in the various channels. The embodiments described above took very small volumes of solution ($\approx$100 pl) from reservoirs 12 and 40 and accurately injected them into the separation channel 34. For these various scenarios, a given volume of solution needs to be transferred from one channel to another. For example, solvent programming for liquid chromatography or reagent addition for post-column labeling reactions requires that streams of solutions be mixed in precise and known concentrations.

The mixing of various solvents in known proportions can be done according to the present invention by controlling potentials which ultimately control electroosmotic flows as indicated in equation 1. According to equation 1 the electric field strength needs to be known to determine the linear velocity of the solvent. In general, in these types of fluidic manipulations a known potential or voltage is applied to a given reservoir. The field strength can be calculated from the applied voltage and the characteristics of the channel. In addition, the resistance or conductance of the fluid in the channels must also be known.

The resistance of a channel is given by equation 2 where R is the resistance, $\rho$ is the resistivity, L is the length of the channel, and A is the cross-sectional area.

$$R_i = \frac{\rho_i L_i}{A_i} \tag{2}$$

Fluids are usually characterized by conductance which is just the reciprocal of the resistance as shown in equation 3. In equation 3, K is the electrical conductance, $\kappa$ is the conductivity, A is the cross-sectional area, and L is the length as above.

$$K_i = \frac{\kappa_i A_i}{L_i} \tag{3}$$

Using ohms law and equations 2 and 3 we can write the field strength in a given channel, i, in terms of the voltage drop across that channel divided by its length which is equal to the current, $I_i$ through channel i times the resistivity of that channel divided by the cross-sectional area as shown in equation 4.

$$E_i = \frac{V_i}{L_i} = \frac{I_i \rho_i}{A_i} = \frac{I_i}{\kappa_i A_i} \tag{4}$$

Thus, if the channel is both dimensionally and electrically characterized, the voltage drop across the channel or the current through the channel can be used to determine the solvent velocity or flow rate through that channel as, expressed in equation 5. It is also noted that fluid flow depends on the zeta potential of the surface and thus on the chemical make-ups of the fluid and surface.

$$V_i \propto I_i \propto \text{Flow}$$

Obviously the conductivity, $\kappa$, or the resistivity, $\rho$, will depend upon the characteristics of the solution which could vary from channel to channel. In many CE applications the characteristics of the buffer will dominate the electrical characteristics of the fluid, and thus the conductance will be constant. In the case of liquid chromatography where solvent programming is performed, the electrical characteristics of the two mobile phases could differ considerably if a buffer is not used. During a solvent programming run where the mole fraction of the mixture is changing, the conductivity of the mixture may change in a nonlinear fashion but it will change monotonically from the conductivity of the one neat solvent to the other. The actual variation of the conductance with mole fraction depends on the dissociation constant of the solvent in addition to the conductivity of the individual ions.

As described above, the device shown schematically in FIG. 31 could be used for performing gradient elution liquid chromatography with post-column labeling for detection purposes, for example. FIG. 31(a), 31(b), and 31(c) show the fluid flow requirements for carrying out the tasks involved in a liquid chromatography experiment as mentioned above. The arrows in the figures show the direction and relative magnitude of the flow in the channels. In FIG. 31(a), a volume of analyte from the analyte reservoir 16 is loaded into the separation intersection 40. To execute a pinched injection it is necessary to transport the sample from the analyte reservoir 16 across the intersection to the analyte waste reservoir 18. In addition, to confine the analyte volume, material from the separation channel 34 and the solvent reservoirs 12,14 must flow towards the intersection 40 as shown. The flow from the first reservoir 12 is much larger than that from the second reservoir 14 because these are the initial conditions for a gradient elution experiment. At the beginning of the gradient elution experiment, it is desirable to prevent the reagent in the reagent reservoir 22 from entering the separation channel 34. To prevent such reagent flow, a small flow of buffer from the waste reservoir 20 directed toward the reagent channel 36 is desirable and this flow should be as near to zero as possible. After a representative analyte volume is presented at the injection intersection 40, the separation can proceed.

In FIG. 31(b), the run (separation) mode is shown, solvents from reservoirs 12 and 14 flow through the intersection 40 and down the separation channel 34. In addition, the solvents flow towards reservoirs 4 and 5 to make a clean injection of the analyte into the separation channel 34. Appropriate flow of reagent from the reagent reservoir 22 is also directed towards the separation channel. The initial condition as shown in FIG. 31(b) is with a large mole fraction of solvent 1 and a small mole fraction, of solvent 2. The voltages applied to the solvent reservoirs 12, 14 are changed as a function of time so that the proportions of solvents 1 and 2 are changed from a dominance of solvent 1 to mostly solvent 2. This is shown in FIG. 31(c). The latter monotonic change in applied voltage effects the gradient elution liquid chromatography experiment. As the isolated components pass the reagent addition channel 36, appropriate reaction can take place between this reagent and the isolated material to form a detectable species.

Figure 32:
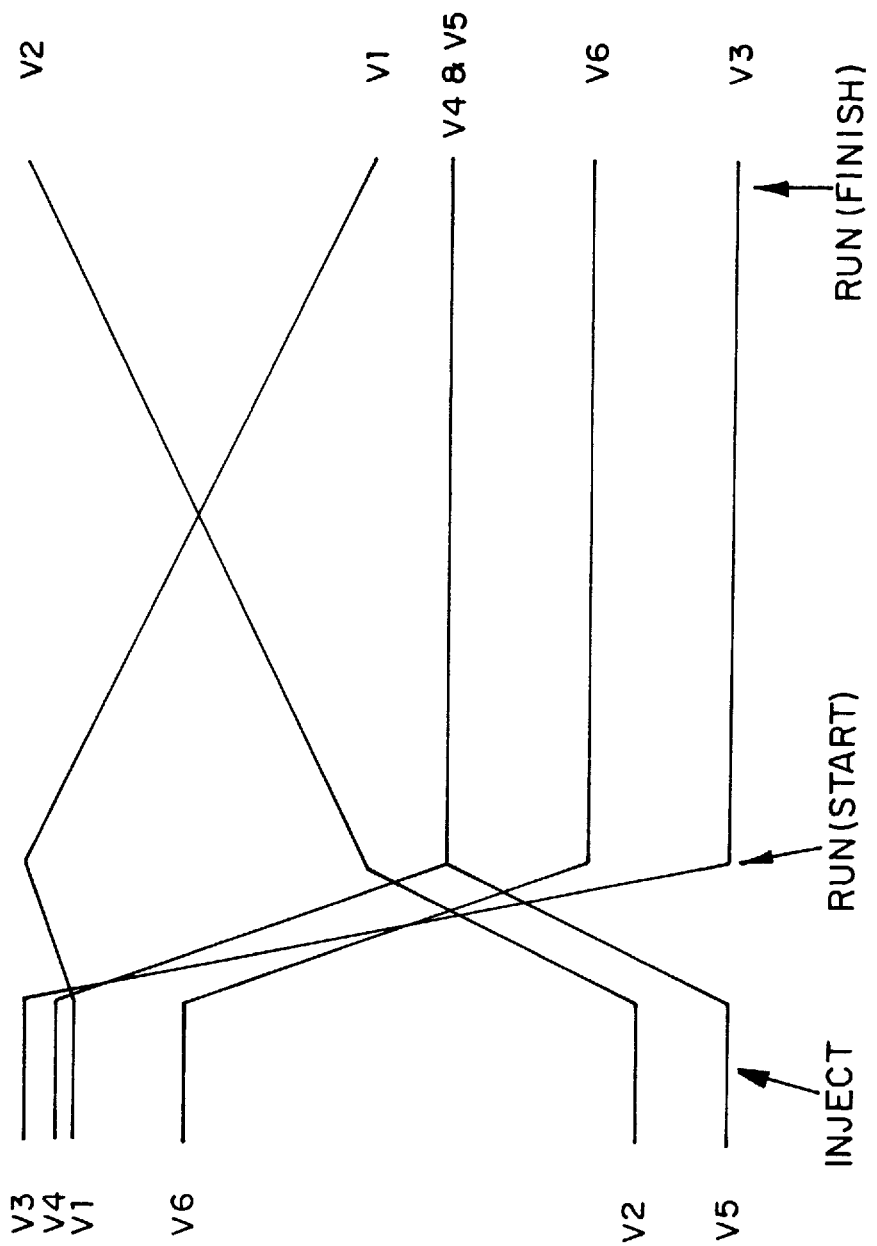
FIG. 32 is a graph showing the different voltages applied to effect the fluidic manipulations of FIG. 23.

FIG. 32 shows how the voltages to the various reservoirs are changed for a hypothetical gradient elution experiment. The voltages shown in this diagram only indicate relative magnitudes and not absolute voltages. In the loading mode of operation, static voltages are applied to the various reservoirs. Solvent flow from all reservoirs except the reagent reservoir 22 is towards the analyte waste reservoir 18. Thus, the analyte reservoir 18 is at the lowest potential and all the other reservoirs are at higher potential. The potential at the reagent reservoir should be sufficiently below that of the waste reservoir 20 to provide only a slight flow towards the reagent reservoir. The voltage at the second solvent reservoir 14 should be sufficiently great in magnitude to provide a net flow towards the injection intersection 40, but the flow should be a low magnitude.

In moving to the run (start) mode depicted in FIG. 31(b), the potentials are readjusted as indicated in FIG. 32. The flow now is such that the solvent from the solvents reservoirs 12 and 14 is moving down the separation channel 34 towards the waste reservoir 20. There is also a slight flow of solvent away from the injection intersection 40 towards the analyte and analyte waste reservoirs 16 and 18 and an appropriate flow of reagent from the reagent reservoir 22 into the separation channel 34. The waste reservoir 20 now needs to be at the minimum potential and the first solvent reservoir 12 at the maximum potential. All other potentials are adjusted to provide the fluid flow directions and magnitudes as indicated in FIG. 31(b). Also, as shown in FIG. 32, the voltages applied to the solvent reservoirs 12 and 14 are monotonically changed to move from the conditions of a large mole fraction of solvent 1 to a large mole fraction of solvent 2.

At the end of the solvent programming run, the device is now ready to switch back to the inject condition to load another sample. The voltage variations shown in FIG. 32 are only to be illustrative of what might be done to provide the various fluid flows in FIGS. 31(a)–(c). In an actual experiment some to the various voltages may well differ in relative magnitude.

While advantageous embodiments have been chosen to illustrate the invention, it will be understood by those skilled in the art that various changes and modifications can be made therein without departing from the scope of the invention as defined in the appended claims.

I claim:

1. A microchip laboratory system for analyzing or synthesizing chemical material, comprising:

a body having disposed therein, a plurality of integrated channels connecting a plurality of at least five reservoirs, at least one reservoir having at least a first material disposed therein, and each of at least five of the reservoirs simultaneously having separate controlled electrical potentials associated therewith, said electrical potentials presenting a voltage gradient between one reservoir and at least one other reservoir, to transport said first material from said at least one other reservoir through at least one of the plurality of integrated channels toward at least one of the other reservoirs to expose said first material to one or more selected chemical or physical environments.

2. The system of claim 1, wherein said first material is a fluid.

3. The system of claim 1, wherein said plurality of integrated channels comprises:

at least three of said plurality of integrated channels in fluid communication at a first intersection, each of said at least three channels connecting said first intersection with a separate one of at least three of the reservoirs; and wherein said electrical potentials simultaneously associated with said at least three reservoirs simultaneously transport materials from at least two of the reservoirs to the first intersection, to mix the materials from the at least two reservoirs at the first intersection.

4. The system of claim 3, wherein an electrical potential at the first intersection is less than the electrical potential associated with each of the at least two reservoirs.

5. The system of claim 1, wherein said plurality of integrated channels comprises:

at least first, second, third, and fourth channels in fluid communication at a first intersection, said first, second, third, and fourth channels connecting first, second, third and fourth reservoirs to said intersection respectively; and wherein said electrical potential controls the volume of a first material transported from the first reservoir to the second reservoir through the first intersection by transporting a second material from the third reservoir through the first intersection.

6. The system of claim 5, wherein the electrical potential selectively transports the second material from the third reservoir through the first intersection toward the second or fourth reservoirs.

7. The system of claim 5, wherein the electrical potentials transport the second material through the first intersection preventing the first material from moving through the first intersection toward the second reservoir, after a selected volume of the first material has passed the first intersection toward the second reservoir.

8. The system of claim 5, wherein the electrical potentials transport the first and second materials into the first intersection and toward the second reservoir.

9. The system of claim 1, wherein the plurality of integrated channels comprises:
   a first channel connecting a first and a second of said at least five reservoirs, a second channel connecting a third and a fourth of said at least five reservoirs the first channel and the second channel intersecting at a first intersection; and
   a third channel connecting a fifth of the at least five reservoirs, with the second channel at a location between the first intersection and the fourth reservoir.

10. The system of claim 9, wherein said electrical potentials simultaneously transport material from the fifth reservoir and material from the first intersection toward the fourth reservoir, to mix the materials from the first intersection and the fifth reservoir.

11. The system of claim 9 wherein the third channel connects the fifth reservoir with a sixth reservoir, the third channel intersecting the second channel; at a second intersection the second intersection being located at a point on the third channel between the fifth and sixth reservoirs.

12. The system of claim 11, wherein the electrical potentials simultaneously transport material from the fifth and sixth reservoirs into the second intersection.

13. The system of claim 12, wherein the electrical potentials transport material from the firth and sixth reservoirs through the second intersection toward the first intersection and toward the fourth reservoir, after a selected volume of material from the first intersection is transported through the second intersection toward the fourth reservoir.

14. A microchip flow system, comprising:
   a body having first and second channels disposed therein the first channel connecting first and second reservoirs, the first reservoir having a first material disposed therein, and the second channel connecting third and fourth reservoirs, the first channel intersecting the second channel at a point on the first channel between the first and second reservoirs to form a first intersection, and in which at least three of the reservoirs simultaneously have controlled electrical potentials associated therewith said electrical potentials effecting transport of a volume of first material from the first reservoir to the second reservoir through the first intersection, said volume being selectively controlled by the movement of a material from the third reservoir through the first intersection toward another reservoir.

15. The system of claim 14 wherein the first material is a fluid.

16. The system of claim 14 wherein the electrical potentials transport a second material from the third reservoir through the first intersection toward the second reservoir.

17. The system of claim 15 wherein the electrical potentials transport the second material from the third reservoir through the first intersection toward the fourth reservoir preventing the first material from moving through the first intersection toward the second reservoir after a selected volume of the first material has passed through the first intersection toward the second reservoir.

18. The system of claim 15 electrical potentials simultaneously transport the first and second materials from the first intersection toward the second reservoir.

19. The system of claim 14 further comprising a third channel that connects a fifth reservoir with the first channel at a location between the first intersection and the second reservoir.

20. The system of claim 19, further comprising: an additional electrical potential associated with the fifth reservoir, the additional electrical potential transporting material from the fifth reservoir with material transported from the first intersection toward the second reservoir.

21. The system of claim 19, further comprising a sixth reservoir having a controlled electrical potential associated therewith, the third channel connecting the fifth and sixth reservoirs and crossing the first channel at a second intersection between the firth and sixth reservoirs.

22. The system of claim 21, further wherein the electrical potentials simultaneously transport material from the fifth and sixth reservoirs into the second intersection.

23. The system of claim 21, wherein the electrical potentials simultaneously transport material from the fifth and sixth reservoirs through the second intersection and toward the second reservoir.

24. A microflow control system, comprising a body having integrated channels connecting at least four reservoirs, wherein first and second reservoirs of the four reservoirs contain first and second materials, respectively, a channel connecting the first reservoir and a third reservoir forming an intersection with a channel connecting the second and a fourth reservoir; and
   a voltage controller that:
      applies an electrical potential difference between the first reservoir and the third reservoir, and selectively applies a potential difference between the second and fourth reservoirs or the second and third reservoirs to transport a selected, variable volume of the first material from the first reservoir through the intersection toward the third reservoir.

25. A method of controlling the flow of material through an interconnected channel system having at least first and second channels and at least four reservoirs, the first channel connecting first and third reservoirs and the second channel connecting second and fourth reservoirs, wherein the first reservoir contains a first material, the first channel intersecting the second channel at a first intersection between the first and third reservoirs, the method comprising:
   applying an electrical potential difference between the first reservoir and the third reservoir in a manner that transports a selected, variable volume of the first material from the first reservoir through the intersection toward the third reservoir; and
   after a selected time period, simultaneously applying a selected electrical potential to each of at least three of the four reservoirs in a manner that inhibits the movement of the first material through the intersection toward the third reservoir.

* * * * *

UNITED STATES PATENT AND TRADEMARK OFFICE
CERTIFICATE OF CORRECTION

PATENT NO. : 5,858,195
DATED : January 12, 1999
INVENTOR(S) : J. Michael Ramsey

It is certified that error appears in the above-identified patent and that said Letters Patent is hereby corrected as shown below:

Column 35, claim 13,
Line 47, "firth" should be -- fifth --;

Column 36, claim 18,
Line 11, after "claim15" insert -- wherein the --;

Column 36, claim 21,
Line 27, "firth" should be -- fifth --;

Signed and Sealed this

Twelfth Day of March, 2002

Attest:

Attesting Officer

JAMES E. ROGAN
Director of the United States Patent and Trademark Office